(12) United States Patent
Drake et al.

(10) Patent No.: US 9,109,080 B2
(45) Date of Patent: *Aug. 18, 2015

(54) CROSS-LINKED ORGANIC POLYMER COMPOSITIONS AND METHODS FOR CONTROLLING CROSS-LINKING REACTION RATE AND OF MODIFYING SAME TO ENHANCE PROCESSABILITY

(71) Applicant: Delsper LP, Kulpsville, PA (US)

(72) Inventors: Kerry A. Drake, Red Hill, PA (US); Andrew F. Nordquist, Whitehall, PA (US); Sudipto Das, Norristown, PA (US); William F. Burgoyne, Jr., Bethlehem, PA (US); Le Song, Chalfont, PA (US); Shawn P. Williams, North Wales, PA (US); Rodger K. Boland, Levittown, PA (US)

(73) Assignee: Delsper LP, Kulpsville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/059,064

(22) Filed: Oct. 21, 2013

(65) Prior Publication Data

US 2014/0284850 A1    Sep. 25, 2014

Related U.S. Application Data

(60) Provisional application No. 61/833,351, filed on Jun. 10, 2013, provisional application No. 61/716,800, filed on Oct. 22, 2012.

(51) Int. Cl.
*C08G 65/48* (2006.01)
*C08G 16/00* (2006.01)
(Continued)

(52) U.S. Cl.
CPC ............... *C08G 65/00* (2013.01); *C07C 35/38* (2013.01); *C07C 43/275* (2013.01); *C08G 65/48* (2013.01); *C08L 71/00* (2013.01)

(58) Field of Classification Search
None
See application file for complete search history.

(56) References Cited

U.S. PATENT DOCUMENTS 3,092,191 A    6/1963 Austin et al.
3,512,592 A    5/1970 Kellner (Continued)

FOREIGN PATENT DOCUMENTS

EP    0251357 B1    1/1988
GB    2185114    7/1987

(Continued)

OTHER PUBLICATIONS

Ladacki et al, "Studies of the Variations in Bond Dissociation Energies of Aromatic Compounds. I. Mono-bromo-aryles," Proc. R. Soc. Lond. a, r 219, pp. 341-253 (1953).

(Continued)

*Primary Examiner* — Robert S Loewe
(74) *Attorney, Agent, or Firm* — Flaster/Greenberg P.C.

(57) ABSTRACT

The invention includes a cross-linking composition comprising a cross-linking compound and a cross-linking reaction additive selected from an organic acid and/or an acetate compound, wherein the cross-linking compound has the structure according to formula (IV):

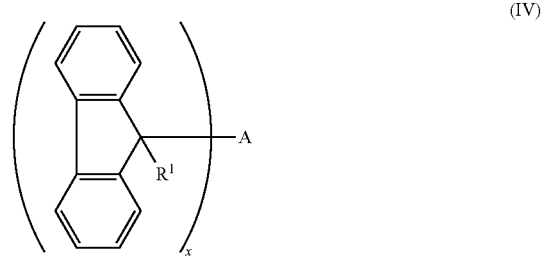

wherein the cross-linking reaction additive is capable of reacting with the cross-linking compound to form a reactive oligomer intermediate, which is capable of cross-linking an organic polymer. Also included is an organic polymer composition for use in forming a cross-linked organic polymer, comprising a cross-linking compound of Formula (IV), a cross-linking reaction additive and at least one organic polymer. In one embodiment, the at least one organic polymer has at least one halogen-containing reactive group and is dehalogenated by reacting with an alkali metal compound. Methods for making such compositions as well as articles of manufacture formed from such methods and organic polymer compositions, wherein the compositions and methods control the cross-linking reaction rate of a crosslinking compound for use in cross-linking an organic polymer are also included.

65 Claims, 7 Drawing Sheets

(51) Int. Cl.
    *C08G 65/00* (2006.01)
    *C07C 35/38* (2006.01)
    *C07C 43/275* (2006.01)
    *C08L 71/00* (2006.01)

(56) References Cited

U.S. PATENT DOCUMENTS

| | | | | |
|---|---|---|---|---|
| 3,533,997 | A | * | 10/1970 | Angelo ............... 525/436 |
| 4,609,714 | A | | 9/1986 | Harris et al. |
| 4,708,994 | A | | 11/1987 | Wong |
| 4,710,948 | A | | 12/1987 | Withjack |
| 4,731,442 | A | | 3/1988 | Lindley et al. |
| 4,827,761 | A | | 5/1989 | Vinegar et al. |
| 4,861,810 | A | | 8/1989 | Dewhirst |
| 5,108,840 | A | | 4/1992 | Mercer |
| 5,114,780 | A | | 5/1992 | Mercer et al. |
| 5,134,207 | A | | 7/1992 | McGrath et al. |
| 5,145,936 | A | | 9/1992 | Mercer |
| 5,155,175 | A | * | 10/1992 | Mercer et al. ........... 525/390 |
| 5,173,542 | A | | 12/1992 | Lau et al. |
| 5,179,188 | A | | 1/1993 | Mercer et al. |
| 5,204,416 | A | | 4/1993 | Mercer et al. |
| 5,235,044 | A | | 8/1993 | Mercer et al. |
| 5,270,453 | A | | 12/1993 | Lau et al. |
| 5,658,994 | A | | 8/1997 | Burgoyne, Jr. et al. |
| 5,668,245 | A | | 9/1997 | Marrocco, III et al. |
| 5,886,130 | A | | 3/1999 | Trimmer et al. |
| 6,060,170 | A | | 5/2000 | Burgoyne, Jr. |
| 6,184,284 | B1 | | 2/2001 | Stokich, Jr. et al. |
| 6,339,966 | B1 | | 1/2002 | Kalidindi |
| 6,582,251 | B1 | | 6/2003 | Burke et al. |
| 6,716,955 | B2 | | 4/2004 | Burgoyne, Jr. |
| 6,855,774 | B2 | | 2/2005 | Kawasaki et al. |
| 6,878,778 | B1 | | 4/2005 | Kawasaki et al. |
| 6,914,119 | B2 | | 7/2005 | Yoshida et al. |
| 7,001,678 | B2 | | 2/2006 | Casasabta, III et al. |
| 7,087,701 | B2 | | 8/2006 | Londergan |
| 7,101,957 | B2 | | 9/2006 | Huang et al. |
| 7,109,249 | B2 | | 9/2006 | Bruza et al. |
| 7,115,531 | B2 | | 10/2006 | Shaffer, II et al. |
| 7,189,795 | B2 | | 3/2007 | Burgyyne, Jr. et al. |
| 7,196,155 | B2 | | 3/2007 | Chen et al. |
| 7,249,971 | B2 | | 7/2007 | Burke et al. |
| 7,307,137 | B2 | | 12/2007 | Lau et al. |
| 7,589,228 | B2 | | 9/2009 | Nishichi et al. |
| 7,696,275 | B2 | | 4/2010 | Slay et al. |
| 7,919,825 | B2 | | 4/2011 | Kretz et al. |
| 8,096,353 | B2 | | 1/2012 | Ver Meer |
| 8,367,776 | B2 | | 2/2013 | Noguchi et al. |
| 8,502,401 | B2 | | 8/2013 | Burgoyne, Jr. et al. |
| 2002/0195739 | A1 | | 12/2002 | Bagley et al. |
| 2003/0032339 | A1 | | 2/2003 | Bell et al. |
| 2005/0161212 | A1 | | 7/2005 | Leismer et al. |
| 2006/0199910 | A1 | | 9/2006 | Walton et al. |
| 2007/0142547 | A1 | | 6/2007 | Vaidya et al. |
| 2007/0296101 | A1 | | 12/2007 | DiPietro et al. |
| 2010/0022718 | A1 | * | 1/2010 | Tu et al. ............. 525/471 |
| 2010/0081007 | A1 | | 4/2010 | Zheng et al. |
| 2010/0126266 | A1 | | 5/2010 | Coenen |
| 2011/0139466 | A1 | | 6/2011 | Chen et al. |
| 2011/0260343 | A1 | | 10/2011 | Burgoyne, Jr. et al. |
| 2012/0077935 | A1 | | 3/2012 | Gurevich et al. |
| 2012/0097194 | A1 | | 4/2012 | Mcdaniel et al. |
| 2012/0100379 | A1 | | 4/2012 | Luo et al. |
| 2012/0130041 | A1 | * | 5/2012 | Han et al. ............. 528/125 |
| 2012/0252218 | A1 | | 10/2012 | Kori et al. |
| 2013/0012635 | A1 | | 1/2013 | Ren et al. |
| 2013/0130529 | A1 | * | 5/2013 | Ayers ............. 439/271 |
| 2014/0213742 | A1 | | 7/2014 | Drake et al. |
| 2014/0316079 | A1 | | 10/2014 | Drake et al. |

FOREIGN PATENT DOCUMENTS

| | | |
|---|---|---|
| WO | WO 0061667 A1 | 10/2000 |
| WO | WO 01/16232 A1 | 3/2001 |
| WO | WO 2009021999 A1 | 2/2009 |
| WO | WO 2010/019488 A1 | 2/2010 |
| WO | WO 2011071619 A2 | 6/2011 |
| WO | WO 2013074120 A1 | 5/2013 |

OTHER PUBLICATIONS

C.-M. Chan et al., "Crosslinking of Poly(arylene ether ketones). II. Crystallization Kinetics," J. of Polymer Science: Part B: Polymer Physics, vol. 25, pp. 1655-1665 (1987).

Hendrick, "Elastomeric behavior of Crosslinked poly(aryl ether ketone)s at elevated temperatures," Polymer, vol. 22, No. 23, pp. 5094-5097, (1992). Butterworth-Heinimann Ltd.

Yi-Chi Chien et al, "Fate of Bromine in Pyrolysis of Printed Circuit Board Wastes," ChemoSphere, vol. 40, pp. 383-387 (2000).

Burke et al., "High Pressure/High Temperature Technology and Introduction of LHT a New High Temperature Plastic," MERL, 26 pages (Sep. 2010).

Drake, "High Temperature Hybrid Elastomers," PhD Thesis, (2011).

International Search Report and Written Opinion for PCT/US13/65977, mailed Apr. 17, 2014—15 pages.

International Search Report and Written Opinion for PCT/US14/13246, mailed Apr. 30, 2014—16 pages.

International Search Report and Written Opinion for PCT/US14/30666, mailed Aug. 13, 2014—19 pages.

Written Opinion for PCT/US14/30666, mailed Jan. 30, 2015—3 pages.

* cited by examiner

CROSS-LINKED ORGANIC POLYMER COMPOSITIONS AND METHODS FOR CONTROLLING CROSS-LINKING REACTION RATE AND OF MODIFYING SAME TO ENHANCE PROCESSABILITY

CROSS-REFERENCE TO RELATED APPLICATIONS SECTION

This application claims the benefit under 35 U.S.C. §119 (e) to U.S. Provisional Patent Applications Nos. 61/833,351, filed Jun. 10, 2013, entitled, "Cross-Linked Organic Polymer Compositions and Methods of Modifying Same to Enhance Processability" and 61/716,800, filed Oct. 22, 2013, entitled; "Cross-Linked Organic Polymer Compositions and Methods for Controlling Cross-Linking Reaction Rate for Forming the Same."

BACKGROUND OF THE INVENTION

1. Field of the Invention

The present invention relates to cross-linked organic polymers, including those having aromatic groups within the polymer chain, and cross-linking compositions and methods for making such polymers. More particularly, it relates to methods for controlling the cross-linking reaction rate of the cross-linking compounds in such compositions to form high glass transition temperature organic polymers, and to methods for enhancing processability of such cross-linked organic polymers and polymer compositions in forming molded parts which may be used, for example, in down-hole tool applications.

2. Description of Related Art

High glass transition temperature polymers have been useful for a number of high temperature applications. Modification of such high glass transition organic polymers generally improves high temperature performance, strength and chemical resistance for use as parts and articles of manufacture necessary in extreme temperature environments as compared to unmodified organic polymers.

Cross-linking has been widely recognized as one way to modify high temperature polymeric materials. Several inventions have been aimed at improving the high temperature performance of organic polymers, such as those having aromatic groups in the backbone, by using cross-linking within the polymers by cross-linking to itself, grafting cross-linking compounds to the polymer, or incorporating cross-linking compounds into the polymer such as by blending.

U.S. Pat. No. 5,874,516, which is assigned to the Applicant of the present application and is incorporated herein by reference in relevant part, shows poly(arylene ether) polymers that are thermally stable, have low dielectric constants, low moisture absorption and low moisture outgassing. The polymers further have a structure that may cross-link to itself or can be cross-linked using a cross-linking agent.

U.S. Pat. No. 6,060,170, which is also assigned to the Applicant of the present application and is incorporated herein by reference in relevant part, describes the use of poly(arylene ether) polymer compositions having aromatic groups grafted on the polymer backbone, wherein the grafts allow for cross-linking of the polymers in a temperature range of from about 200° C. to about 450° C. This patent discloses dissolving the polymer in an appropriate solvent for grafting the cross-linking group. Such required process steps can sometimes make grafting difficult or not practical in certain types of polymers or in certain polymeric structures, including, e.g., polyetherether ketone (PEEK).

International Patent Application Publication No. WO 2010/019488 A1, which is also assigned to the Applicant of the present application and is incorporated herein by reference in relevant part, shows per(phenylethynyl) arene polymers that are grafted to a second polymer to provide a cross-linked polymeric network.

Previous attempts have also been made to control where crosslinks form along the backbone of high glass transition polymers to garner the desired mechanical properties and high temperature performance. U.S. Pat. No. 5,658,994, of Applicant, incorporated herein by reference in relevant part, demonstrates the use of a poly(arylene ether) in low dielectric interlayers which may be cross-linked, for example, by cross-linking the polymer to itself, through exposure to temperatures of greater than about 350° C. or alternatively by using a cross-linking agent. In this patent and as mentioned in U.S. Pat. No. 5,874,516, cross-linking occurs at the ends of the polymer backbone using known end capping agents, such as phenylethynyl, benzocyclobutene, ethynyl, and nitrite. The degree of cross-linking can be limited with the results of a lower glass transition temperature, reduced chemical resistance and lesser tensile strength.

International Patent Application Publication No. WO 20130/74120 A1 of the Applicant of the present application, also incorporated herein by reference in relevant part, discloses a cross-linking compound as used in the invention described herein, which is blended with an uncrosslinked polymer to achieve a crosslinked organic polymer with a higher glass transition temperature for use in extreme conditions such as in down-hole tool applications.

While cross-linking agents may be effective, there can be difficulty in controlling the rate and extent of cross-linking. Cross-linked organic polymers having aromatic groups in the backbone such as cross-linked polyarylene ether polymers, including cross-linked polyetherether ketone (PEEK), even when made using agents to control cross-linking as described herein are amorphous polymers that function well at high temperature (having a $T_g$ above about 270° C.). The crosslinking provides enhanced chemical resistance to add to the high temperature properties of the base polymers. Cross-linking can be done using techniques as noted in the patents and patent application publications identified above and as described herein using Applicant's techniques. In molding, the controlled cross-linked polymers perform well at about 250° C. (or somewhat below the $T_g$ of the materials). However, as molding temperatures rise, the reaction can accelerate such that full cure may be achieved in less than one minute. Cycle times for injection molded articles, such as tubes, rods or electrical connectors, however, are generally three to five minutes or longer. A full cure in less than a minute can impede the usefulness of conventional molding techniques, such as injection molding or extrusion, in forming molded parts.

Prior art attempts to retard or inhibit and moderate cross-linking reactions using compounds and their reactions are known. See, Vanderbilt Rubber Handbook, 13th ed., 1990, p. 281. However, there is still a need in the art to control and inhibit such reactions, and to improve the ability to process such polymers more easily using traditional molding techniques.

BRIEF SUMMARY OF THE INVENTION

The present invention includes a cross-linking composition comprising a cross-linking compound and a cross-linking reaction additive selected from an organic acid and/or an acetate compound, wherein the cross-linking compound has a structure according to formula (IV):

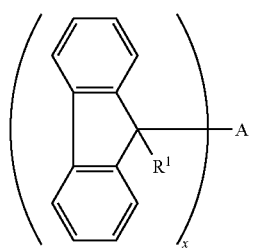

wherein A is an arene moiety having a molecular weight of less than 10,000 g/mol, $R^1$ is selected from a group consisting of hydroxide (—OH), amine (—$NH_2$), halide, ether, ester, or amide, and x=2.0 to 6.0, wherein the cross-linking reaction additive is capable of reacting with the cross-linking compound to form a reactive intermediate in the form of an oligomer, which reactive intermediate oligomer is capable of cross-linking an organic polymer.

The cross-linking compound in the composition as noted above may have a structure according to the following:

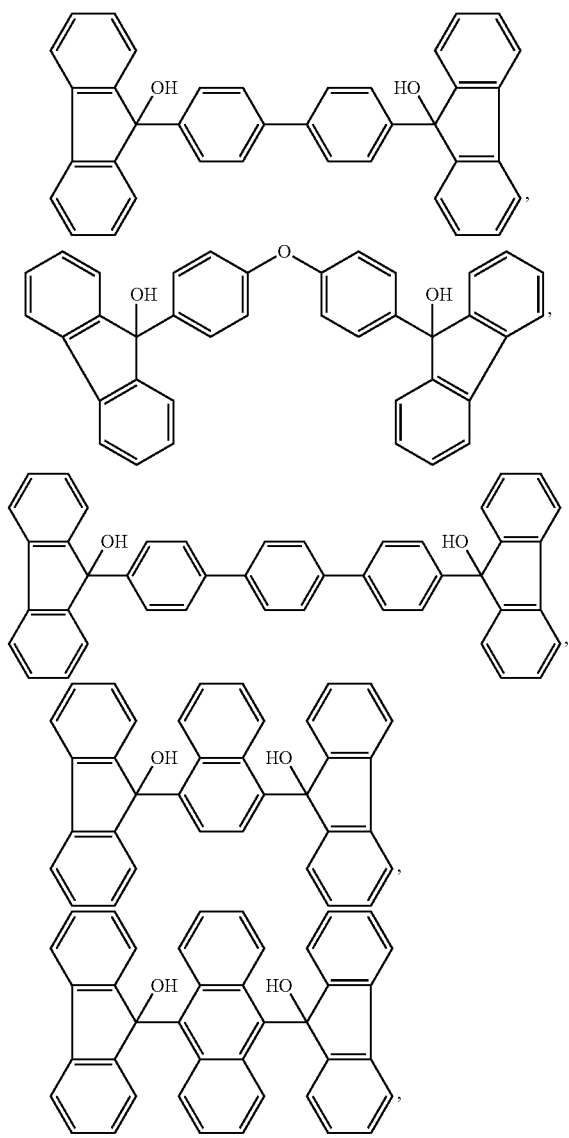

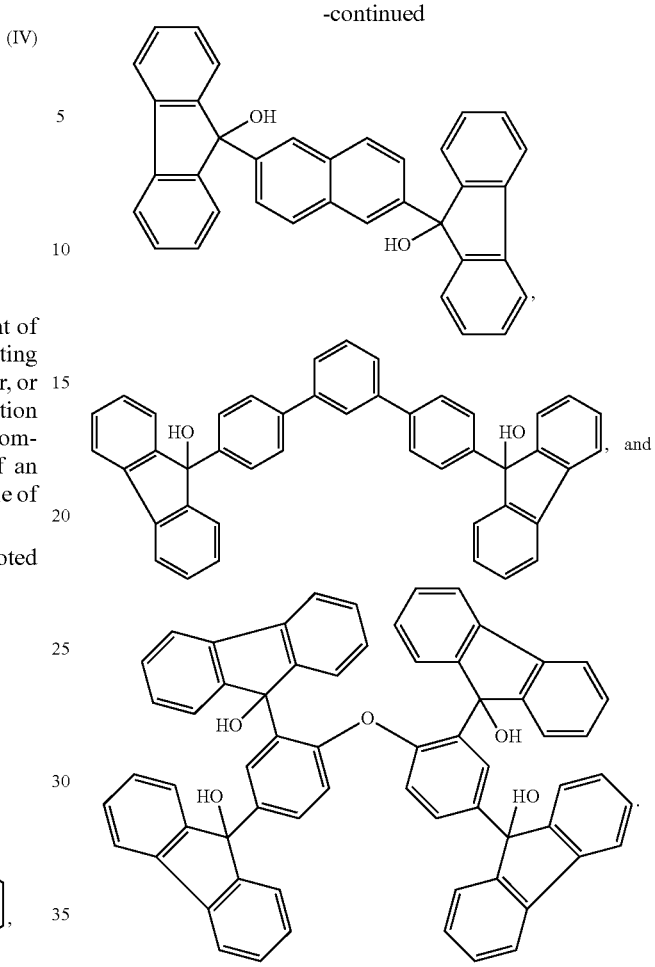

The arene moiety of the cross-linking compound noted above preferably has a molecular weight of about 1,000 g/mol to about 9,000 g/mol, and more preferably about 2,000 g/mol to about 7,000 g/mol.

One inhibitor that works well in crosslinking organic polymers, particularly those with aromatic groups in the backbone, and using a cross-linking compound such as 9,9'-(biphenyl-4,4'-diyl)bis(9H-fluoren-9-ol) shown in formula (I) below, may be, for example, in one embodiment herein, an organic acid such as glacial acetic acid, formic acid, and/or benzoic acid.

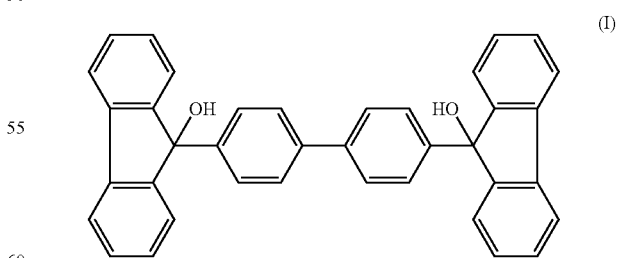

Thus, in one embodiment, the cross-linking reaction additive is an organic acid which may be glacial acetic acid, formic acid, and/or benzoic acid.

In another embodiment, the cross-linking reaction additive may be an acetate compound that has a structure according to formula (II):

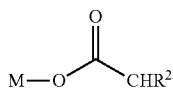

(II)

wherein M is a Group I or a Group II metal; and $R^2$ is an alkyl, aryl, or aralkyl group, wherein the alkyl group is a hydrocarbon group of 1 to about 30 carbon atoms, preferably about 1 to about 15 carbon atoms having 0 to about 10 ester or ether groups along or in the chain of the hydrocarbon group, preferably about 0 to about 5 ester or ether groups, wherein $R^2$ may have 0 to about 10, preferably about 0 to about 5, functional groups that may be one or more of sulfate, phosphate, hydroxyl, carbonyl, ester, halide, mercapto or potassium. More preferably, the acetate compound may be lithium acetate hydrate, sodium acetate and/or potassium acetate, and salts and derivatives thereof.

The weight percentage ratio of the cross-linking compound to the cross-linking reaction additive may be about 10:1 to about 10,000:1, and more preferably about 20:1 to about 1000:1.

In another embodiment, the invention includes an organic polymer composition for use in forming a cross-linked organic polymer, comprising a cross-linking compound having a structure as in formula (IV) as described above; a cross-linking reaction additive selected from an organic acid and/or an acetate compound; and at least one organic polymer, wherein the cross-linking reaction additive is capable of reacting with the cross-linking compound to form a reactive intermediate in the form of an oligomer, which reactive intermediate oligomer is capable of cross-linking the organic polymer.

In a further embodiment, the invention includes an organic polymer composition for use in forming a cross-linked organic polymer, comprising an organic polymer and a reactive cross-linking oligomer which is a reaction product of a cross-linking compound having a structure as in formula (IV) described above and a cross-linking reaction additive selected from an organic acid and/or an acetate compound.

The organic polymer is preferably a polymer selected from poly(arylene ether)s, polysulfones, polyethersulfones, polyimides, polyamides, polyureas, polyurethanes, polyphthalamides, polyamide-imides, poly(benzimidazole)s and polyaramids.

The organic polymer may also be a polymer in one embodiment herein that is a poly(arylene ether) including polymer repeating units along its backbone having the following structure:

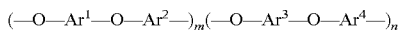

wherein $Ar^1$, $Ar^2$, $Ar^3$ and $Ar^4$ are identical or different aryl radicals, m=0 to 1.0, and n=1−m.

In a further preferred embodiment, the organic polymer is a polymer having an aromatic group in the backbone, preferably a poly(arylene ether), m is 1 and n is 0 and the polymer has repeating units along its backbone having the structure of formula (V):

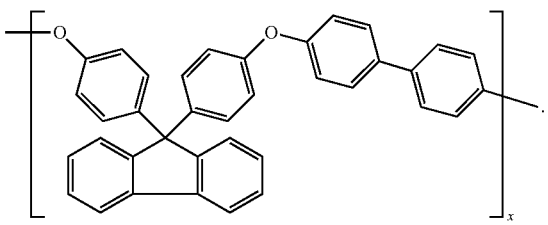

(V)

The cross-linking compound in this embodiment may have the various structures noted above and the arene moiety may also have the characteristics as noted above.

In one embodiment of the invention, the cross-linking reaction additive is an organic acid such as glacial acetic acid, formic acid and/or benzoic acid. In an alternative embodiment of the invention, the cross-linking reaction additive is an acetate compound such as those noted above having the structure according to formula (II). More preferably, the acetate compound is one or more of lithium acetate hydrate, sodium acetate, and/or potassium acetate, and salts and derivatives thereof. The weight percentage ratio of the organic polymer to the combined weight of the cross-linking compound and the cross-linking reaction additive in the composition of this embodiment may be about 1:1 to about 100:1, and is preferably about 3:1 to about 10:1.

The organic polymer composition may further comprise one or more additives. Preferably, the additive(s) is/are selected from one or more of continuous or discontinuous, long or short, reinforcing fibers selected from one or more of carbon fibers, glass fibers, woven glass fibers, woven carbon fibers, aramid fibers, boron fibers, polytetrafluorethylene (PIPE) fibers, ceramic fibers, polyamide fibers, and/or one or more filler(s) selected from carbon black, silicate, fiberglass, calcium sulfate, boron, ceramic, polyamide, asbestos, fluorographite, aluminum hydroxide, barium sulfate, calcium carbonate, magnesium carbonate, silica, aluminum nitride, borax (sodium borate), activated carbon, pearlite, zinc terephthalate, graphite, talc, mica, silicon carbide whiskers or platelets, nanofillers, molybdenum disulfide, fluoropolymer fillers, carbon nanotubes and fullerene tubes.

The additive preferably includes a reinforcing fiber which is a continuous or discontinuous, long or short fiber, that is carbon fiber, polytetrafluoroethylene (PTFE) fiber, and/or glass fiber. Most preferably, the additive is a reinforcing fiber is a continuous long fiber. The organic polymer composition in preferred embodiments comprises about 0.5% to about 65% by weight of additive(s) in the composition and more preferably about 5.0% to about 40% by weight of additive(s) in the composition. The organic polymer composition may further comprise one or more of stabilizers, flame retardants, pigments, colorants, plasticizers, surfactants, and or dispersants.

A method is also provided herein for controlling the cross-linking reaction rate of a cross-linking compound for use in cross-linking an organic polymer. The method comprises providing a cross-linking composition comprising a cross-linking compound and a cross-linking reaction additive selected from an organic acid and/or an acetate compound, wherein the cross-linking compound has a structure according to formula (IV) as noted above, wherein the cross-linking reaction additive is capable of reacting with the cross-linking compound to form a reactive intermediate in the form of an oligomer for cross-linking an organic polymer; and heating the cross-linking composition such that oligomerization of the cross-linking compound occurs.

None embodiment, the method further comprises heating the cross-linking composition before heat molding. In an alternative embodiment, the method further comprises heating the cross-linking composition during heat molding.

The cross-linking compound used in the method may have any of the various structures as noted above. In one embodiment, the cross-linking reaction additive is an organic acid and/or acetate as described above.

In one embodiment, the method further comprises combining the cross-linking compound and the cross-linking reaction additive in a solvent and reacting the cross-linking compound and the cross-linking reaction additive to form a reactive oligomerized cross-linking compound. In an alternative embodiment, the method further comprises combining the cross-linking compound and the cross-linking reaction additive in solid form.

The method of forming an organic polymer composition may also include the steps of adding the reactive oligomerized cross-linking compound to an organic polymer to form a cross-linkable composition, cross-linking the organic polymer composition to form a cross-linked organic polymer. The organic polymer of the method can one of the various polymers noted above, including the preferred polyarylene polymers having a repeating unit as in formula (V).

The present invention also includes heat-molded articles useful for down-hole and other extreme condition end applications which are formed from the organic polymer compositions and methods as described above. The articles may be formed by various methods or techniques including extrusion, injection molding, blow molding, blown film molding, compression molding and/or injection/compression molding. Preferably, the articles include, for example, but are not limited to acid-resistant coatings, chemical-casted films, extruded films, solvent-casted films, blown films, encapsulated products, insulation, packaging, composite cells, connectors, and sealing assemblies in the shape of O-rings, V-rings, U-cups, gaskets, bearings, valve seats, adapters, wiper rings, chevron back-up rings, and tubing.

In addition to use of the compounds noted above, the applicants herein have observed that as viscosity increases in such aromatic group-containing organic polymers, the degree of inhibition which can be achieved from using such cross-linking reaction additives for rate control may not always be sufficient such that in some embodiments herein, additional modification is desirable to improve end effects be reducing and/or controlling the curing and cross-linking rate.

Thus, Applicant has also developed a solution to the need in the art for easier, smooth processing and heat molding of cross-linked organic polymers, either formed using techniques described herein or formed using prior art techniques, allowing for use of traditional molding techniques which require a window of curing which can be longer than what may be achieved using a direct cross-linking process as in the prior art techniques noted above and/or even over and above the inhibition effects achieved using Applicant's enhanced cross-linking reaction additives as described above and elsewhere herein.

Thus, the invention further provides debrominated organic polymers for cross-linking, particularly useful for those organic polymers having an aromatic group in the backbone and/or that are in the category of high glass transition temperature polymers, as well as compositions including such dehalogenated organic polymers and methods for preparing and cross-linking the same. The resulting articles are formed using controlled cross-linking reaction rates enabling use of traditional molding techniques during crosslinking of such polymers due to the enhanced (processability of the dehalogenated organic polymers. The invention opens an avenue for creating a variety of unique and readily moldable cross-linked organic polymer articles of manufacture providing the beneficial properties of such materials, including chemical resistance, high-temperature and high-pressure performance and strength for a variety of end applications.

Included herein is an organic polymer composition for use in forming a cross-linked aromatic polymer, comprising a dehalogenated organic polymer and at least one cross-linking compound. In one embodiment, the dehalogenated organic polymer is a debrominated organic polymer.

In one embodiment, the cross-linking compound has a structure according to formula (IV):

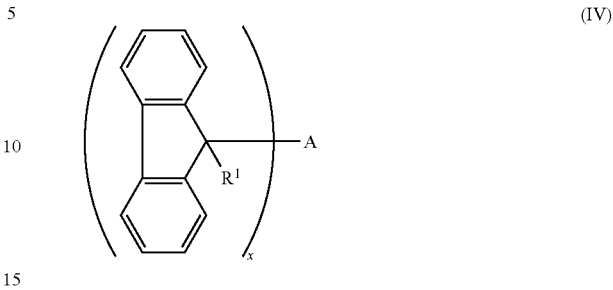

wherein A is an arene moiety having a molecular weight of less than 10,000 g/mol, $R^1$ is selected from a group consisting of hydroxide (—OH), amine (—$NH_2$), halide, ether, ester, or amide, and x is about 2.0 to about 6.0.

In further embodiments, the cross-linking compound has a structure selected from a group consisting of

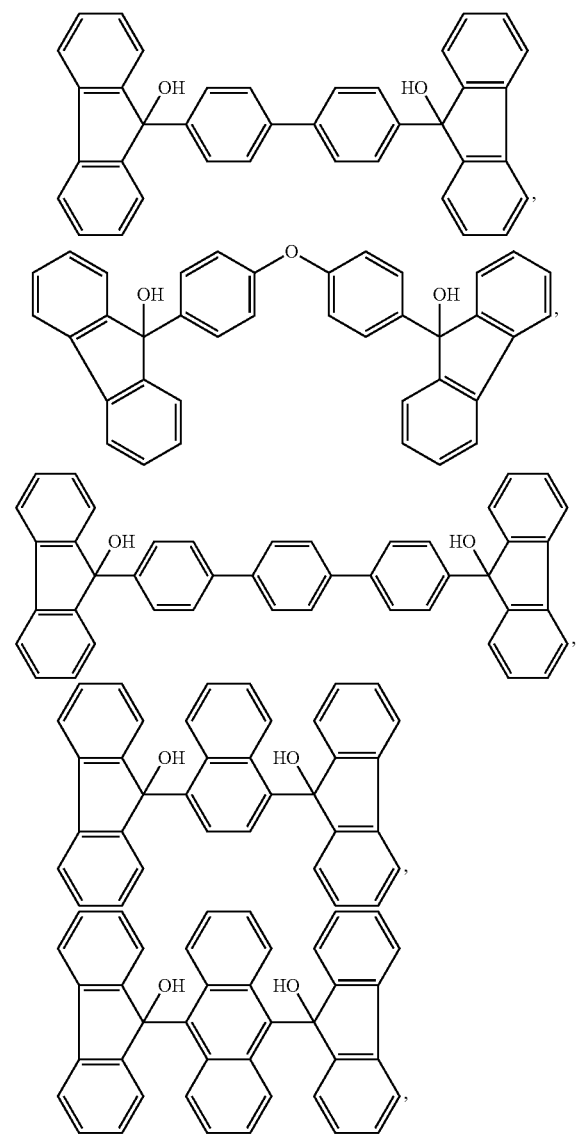

-continued

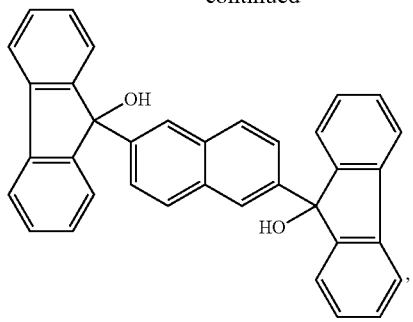

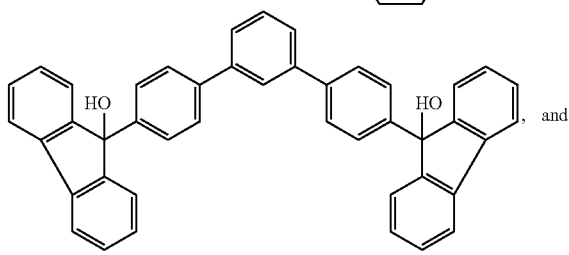, and

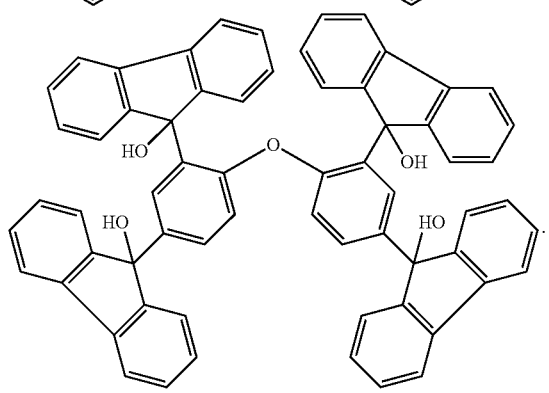.

The arene moiety may have a molecular weight of about 1,000 g/mol to about 9,000 g/mol, or more preferably about 2,000 g/mol to about 7,000 g/mol.

The composition may also further comprise a cross-linking reaction additive selected from an organic acid and/or an acetate compound, wherein the cross-linking reaction additive is capable of reacting with the cross-linking compound to form a reactive intermediate in the form of an oligomer, which reactive intermediate oligomer is capable of cross-linking the dehalogenated organic polymer.

Such a cross-linking reaction additive may be an organic acid selected from glacial acetic acid, formic acid, and/or benzoic acid. The cross-linking reaction additive in a further embodiment is an acetate compound having a structure according to formula (II):

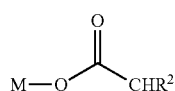 (II)

wherein M is a Group I or a Group II metal; and $R^2$ is a alkyl, aryl or aralkyl group, wherein the alkyl group comprises a hydrocarbon group of 1 to about 30 carbon atoms which has from 0 to about 10 ester or ether groups, preferably 0 to about 5 such groups, along or in a chain or structure of the group, and wherein $R^2$ comprises 0 to about 10 functional groups selected from sulfate, phosphate, hydroxyl, carbonyl, ester, halide, mercapto or potassium.

The acetate compound is preferably selected from lithium acetate hydrate, sodium acetate, and/or potassium acetate, and salts and derivatives thereof.

The weight percentage ratio of the cross-linking compound to the cross-linking reaction additive may preferably be about 10:1 to about 10,000:1, and more preferably about 20:1 to about 1,000:1.

The weight percentage ratio of the dehalogenated organic polymer to a combined weight of the cross-linking compound and the cross-linking reaction additive may be, for example, about 1:1 to about 100:1, and preferably about 3:1 to about 10:1.

The dehalogentated organic polymer is (preferably a polymer selected from poly(arylene ether)s, polysulfones, polyethersulfones, polyimides, polyamides, polyureas, polyurethanes, polyphthalamides, polyamide-imides, poly(benzimidazole)s and polyaramids.

The dehalogenated organic polymer may also be a polymer in one embodiment herein that is a poly(arylene ether) including polymer repeating units along its backbone having the following structure:

$(—O—Ar^1—O—Ar^2—)_m(—O—Ar^3—O—Ar^4—)_n$ wherein $Ar^1$, $Ar^2$, $Ar^3$ and $Ar^4$ are identical or different aryl radicals, m=0 to 1.0, and n=1−m.

In a further preferred embodiment, the dehalogenated organic polymer is a polymer having an aromatic group in the backbone, preferably a poly(arylene ether), m is 1 and n is 0 and the polymer has repeating units along its backbone having the structure of formula (V):

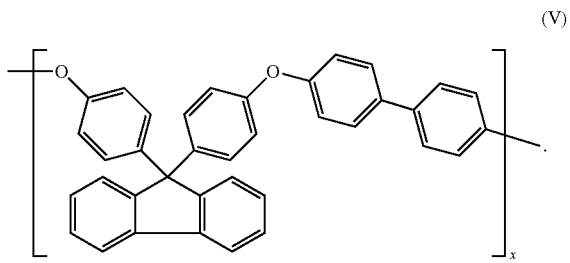 (V)

At least one additive may also be provided to the composition, and the additive(s) may be continuous or discontinuous, long or short, reinforcing fibers selected from carbon fibers, glass fibers, woven glass fibers, woven carbon fibers, aramid fibers, boron fibers, polytetrafluorethylene fibers, ceramic fibers, polyamide fibers; and one or more fillers selected from carbon black, silicate, fiberglass, calcium sulfate, boron, ceramic, polyamide, asbestos, fluorographite, aluminum hydroxide, barium sulfate, calcium carbonate, magnesium carbonate, silica, alumina, aluminum nitride, borax (sodium borate), activated carbon, pearlite, zinc terephthalate, graphite, talc, mica, silicon carbide whiskers or platelets, nanofillers, molybdenum disulfide, fluoropolymer, carbon nanotubes and fullerene tubes.

In one embodiment, the additive(s) comprise reinforcing fibers selected from a group consisting of continuous or discontinuous, long or short, carbon fibers, polytetrafluoroethylene fibers, and glass fibers. If such additives are used as noted above, the composition preferably has about 0.5% to about 65% by weight of the at least one additive, and more preferably about 5.0% to about 40% weight of the at least one additive.

In addition, the composition may further comprise a stabilizer, a flame retardant, a pigment, a plasticizer, a surfactant, and or a dispersant.

The dehalogenated organic polymer is preferably formed, in one embodiment herein, by reacting an organic polymer having at least one halogen-containing reactive group with an alkali metal compound to break the bond between the organic polymer having the at least one halogen-containing reactive group and the halogen atom in the at least one halogen-containing reactive group to form an intermediate having a carbocation. The intermediate having the carbocation is reacted with acetic acid to form the debrominated organic polymer. In one embodiment, the halogen-containing reactive group is a bromine-containing reactive group.

The alkali metal compound useful in such a dehalogenation reaction is preferably one having the structure $R^3$—M', wherein M' is an alkali metal and $R^3$ is H or a branched or straight chain organic group selected from alkyl, alkenyl, aryl and aralkyl groups of from 1 to about 30 carbon atoms having from 0 to about 10 ester or ether groups along or in a chain or structure of the group, and wherein $R^3$ may be substituted or unsubstituted.

The alkali metal compound may in one preferred embodiment herein be t-butyllithium. The organic polymer having at least one halogen-containing end group, such as a bromine-containing reactive group, is preferably reacted with the alkali metal compound in a solvent, and the organic polymer having at least one halogen-containing end group is also preferably dried prior to reacting in the solvent.

The invention also includes molded articles formed from the compositions noted above and described further herein.

The invention also includes a method of controlling the cross-linking reaction rate of an organic polymer having at least one halogen-containing reactive group during a cross-linking reaction, preferably organic polymers having an aromatic group in the backbone chain of the polymer. The method comprises: (a) reacting the organic polymer having at least one halogen-containing reactive group with an alkali metal compound to break the bond between the organic polymer having the at least one halogen-containing reactive group and the halogen atom in the at least one halogen-containing reactive group and thereby forming an intermediate having a carbocation; (b) reacting the intermediate having the carbocation with acetic acid to form a dehalogenated organic polymer; and (c) crosslinking the dehalogenated organic polymer using a crosslinking reaction.

The at least one halogen-containing reactive group is generally a terminal group and the organic polymer may be any of those noted above, such as poly(arylene ether)s, polysulfones, polyethersulfones, polyimides, polyamides, polyureas, polyurethanes, polyphthalamides, polyamide-imides, poly(benzimidazole)s and polyaramids, and is preferably one having an aromatic group in the backbone chain of the polymer. In one embodiment, the organic polymer having the halogen-containing reactive group is poly(arylene ether) including polymer repeating units along its backbone having the following structure:

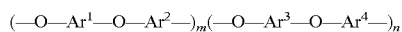

wherein $Ar^1$, $Ar^2$, $Ar^3$ and $Ar^4$ are identical or different aryl radicals, m=0 to 1.0, and n=1−m. In one embodiment, such an organic polymer is a poly(arylene ether), m is 1 and n is 0 and the polymer has repeating units along its backbone having the structure of formula (V):

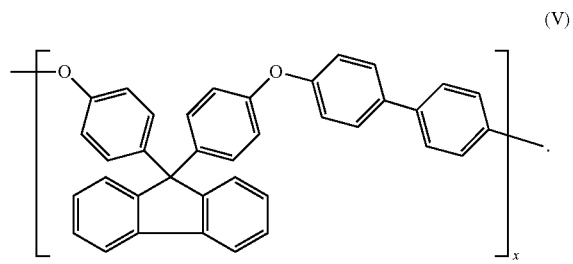

The at least one halogen-containing reactive group is preferably represented by $R^4$—$(X)_p$, wherein $R^4$ is carbon or a branched or straight chain organic group selected from alkyl, alkenyl, aryl and aralkyl groups of from 1 to about 30 carbon atoms having from 0 to about 10 ester or ether groups along or in a chain or structure of the group, preferably from 0 to about 5 of such groups, and wherein $R^4$ may be substituted or unsubstituted; and wherein X is a halogen atom and p is an integer that is 1 or 2.

In one embodiment herein, the alkali metal compound is selected from the group consisting of $R^3$—M', wherein M' is an alkali metal and $R^3$ is H or a branched or straight chain organic group selected from alkyl, alkenyl, aryl and aralkyl groups of from 1 to about 30 carbon atoms having from 0 to about 10 ester or ether groups, preferably 0 to about 5 such groups, along or in a chain or structure of the group, and wherein $R^3$ may be substituted or unsubstituted, and may be t-butyllithium.

The organic polymer having the at least one halogen-containing end group is preferably reacted with the alkali metal compound in a solvent according to an embodiment of the method described herein. The solvent is preferably one which is capable of dissolving the organic polymer having the at least one halogen-containing reactive group and is free of functional groups that react with the halogen in the halogen-containing reacting group under reaction conditions in step (a) noted above. Suitable solvents include a heptane, a hexane, tetrahydrofuran, and a diphenyl ether.

The organic polymer having the at least one halogen-containing end group is also preferably dried prior to reacting with the alkali metal compound in the solvent.

The first reaction step of a dehalogenation treatment preferably occurs at a temperature of less than about −20° C., and more preferably about −70° C. for a period of about 2 hours.

Step (c) of the method noted above, may further comprise: reacting the dehalogenated organic polymer with a cross-linking compound. Such a cross-linking compound has the structure according to formula (IV):

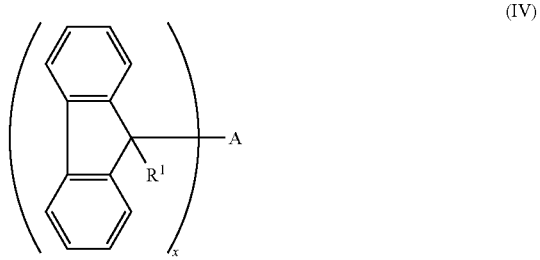

wherein A is an arene moiety having a molecular weight of less than 10,000 g/mol, $R^1$ is selected from a group consisting of hydroxide (—OH), amine (—NH$_2$), halide, ether, ester, or amide, and x is about 2.0 to about 6.0.

Step (c) may also further comprise providing a cross-linking reaction additive selected from an organic acid and/or an acetate compound, wherein the cross-linking reaction additive is capable of reacting with the cross-linking compound to form a reactive intermediate in the form of an oligomer, which reactive intermediate oligomer is capable of cross-linking the dehalogenated organic polymer.

The cross-linking reaction additive may be an organic acid selected from glacial acetic acid, formic acid, and/or benzoic acid. The cross-linking reaction additive may also be an acetate compound having a structure according to formula (II):

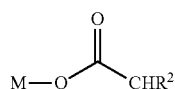

(II)

wherein M is a Group I or a Group II metal; and R$^2$ is a alkyl, aryl or aralkyl group, wherein the alkyl group comprises a hydrocarbon group of 1 to about 30 carbon atoms which has from 0 to about 10 ester or ether groups, preferably 0 to about 5 such groups, along or in a chain or structure of the group, and wherein R$^2$ comprises 0 to about 10 functional groups selected from sulfate, phosphate, hydroxyl, carbonyl, ester, halide, mercapto or potassium.

The acetate compound is preferably selected from lithium acetate hydrate, sodium acetate, and/or potassium acetate, and salts and derivatives thereof.

Step (c) noted above may also include heating the cross-linking compound and the cross-linking reaction additive in a separate composition such that oligomerization of the cross-linking compound occurs to form the reactive intermediate oligomer. The method may also comprise adding the reactive intermediate oligomer to the dehalogenated organic polymer to form a cross-linkable composition and then cross-linking the cross-linkable composition to form a cross-linked organic polymer.

The method may also further comprise heat molding the cross-linked organic polymer to form a heat-molded article of manufacture. The article of manufacture may be formed by heat molding using techniques such as extrusion, injection molding, blow molding, blown film molding, compression molding or injection/compression molding.

The articles of manufacture made herein may be acid-resistant coatings; chemical-casted films; extruded films; solvent-casted films; blown films; encapsulated products; insulation; packaging; composite cells; connectors; sealing assemblies, including O-rings, V-rings, U-cups, gaskets; bearings; valve seats; adapters; wiper rings; chevron back-up rings; and tubing.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
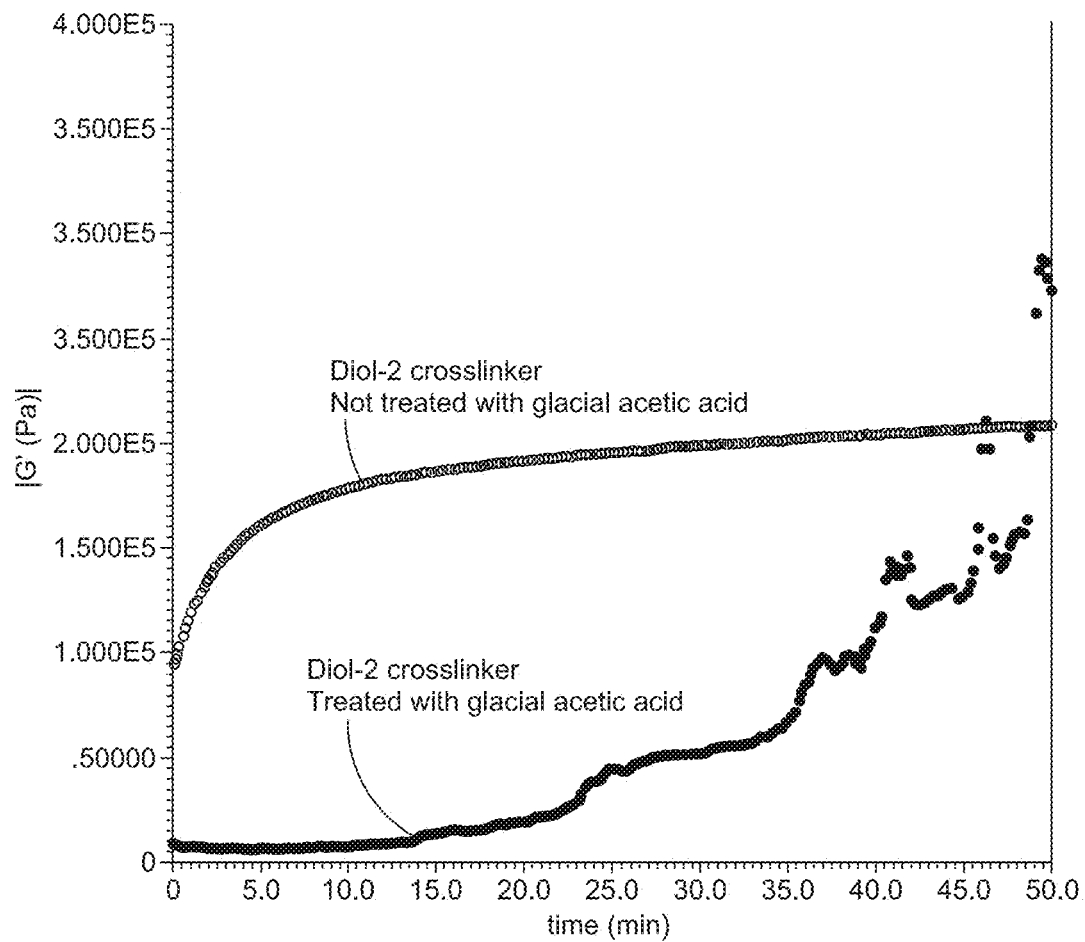
FIG. 1 is a graphical representation of the thermal rate of cure of an organic polymer composition after combination with a product of a cross-linking composition comprising a cross-linking compound and an organic acid.

Described herein are cross-linking compositions that include a cross-linking compound and one or more reactive cross-linking additives, as well as organic polymer compositions for use in forming a cross-linked organic polymer, methods for preparing such compositions and polymers, and articles of manufacture formed from the aforementioned compositions and by such methods which are useful extreme condition end applications such as in down-hole applications.

In the present invention, cross-linking compositions containing a cross-linking compound(s) and a cross-linking reaction additive(s) can be reacted to form a reactive oligomerized cross-linking intermediate either in situ during thermal molding with a cross-linkable organic polymer, and/or by reacting prior to combining with a cross-linkable organic polymer and then heat molding to form an article. This intermediate oligomer reaction product of the cross-linking compound with the crosslinking reaction additive enables control of a cross-linking reaction when combined with an organic polymer and can enable a lower rate of thermal cure, to allow a broader window and better control during heat mold of the resultant cross-linked organic polymer.

Also described herein is a cross-linked organic polymer composition capable of providing an inhibited and/or controlled cross-linking reaction rate and a method for molding articles from cross-linked organic polymers using such composition. The compositions and methods herein enable easier use of traditional (or non-traditional) heat molding techniques to form articles from cross-linked organic compounds without worrying about the window of process formation being inconsistent with the rate of cure, so that premature crosslinking curing is reduced or eliminated during part formation resulting in uniform parts formed from more easy-to-process compositions.

In general, formation of cross-links in an organic polymer cross-linking to itself or in an organic polymer composition comprising an unmodified cross-linking compound may be completed within about 2 minutes at about 380° C., the typical processing temperature of polyetherether ketone (PEEK). The extent of this reaction can be tracked by dynamic viscosity measurements. Two methods are often used to judge when a reaction may be completed. The point where storage modulus G' equals Loss modulus G", called the crossover point or gel point, indicates the onset of gel formation where cross-linking has produced an interconnected. As curing continues, G' will increase, which is an indication of cross-link density. As curing continues, eventually G' will level off, which indicates that most curing is completed. The inflection point G', which indicates onset of vitrification can also be used in cases where no obvious cross-over point can be determined (See FIG. 7). The time required to attain G'; G" crossover or the onset of vitrification can be used as the upper limit of process time for a thermosetting material.

Utilization of one or more cross-linking reaction additive(s) in the invention helps to provide polymers with high glass transition temperatures and high cross-link density. Polymers with high thermal stability of up to 500° C., and high crosslink density, while desirable, display a very high melt viscosity before further processing, and thus are very difficult to melt process. As curing of the cross-linked polymer may be initiated during heat molding, it is desirable to control when cross-linking begins. If the rate of cross-linking is not controlled before molding of a composition into a final article, the article of manufacture may begin to prematurely cure before or during heat molding or proceed too rapidly causing incomplete mold fill, equipment damage, and inferior properties in the article. Thus, the invention improves control of the rate of cross-link formation in an organic polymer. The addition of the cross-linking reaction additive as described herein to the cross-linking compound used for cross-linking organic polymers can delay the onset of cross-linking in the organic polymer for as much as several minutes to allow for rapid processing and shaping of the resultant organic polymer structures in a controlled manner.

One or more cross-linking compounds is/are present in the cross-linking composition and organic polymer compositions herein. Preferably, the cross-linking compound has a structure according to Formula (IV):

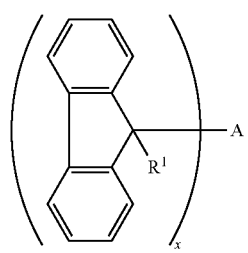

(IV)

wherein A is an arene moiety having a molecular weight of less than 10,000 g/mol. $R^1$ can be hydroxide (—OH), amine (—$NH_2$), halide, ether, ester, or amide, and x is about 2.0 to about 6.0.

The arene moiety A on the cross-linking compound above provides the cross-link site for forming more complex cross-linking compound structures, including, for example, without limitation:

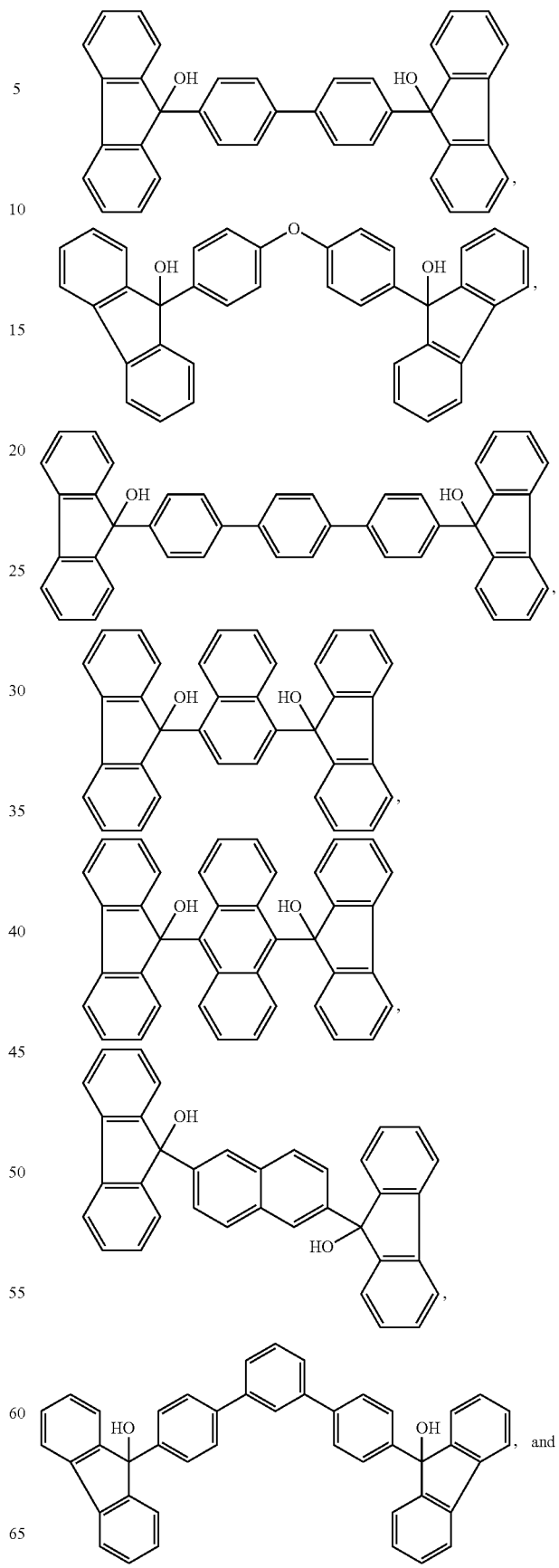

-continued

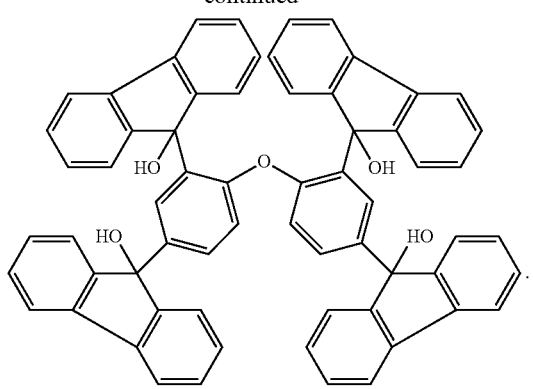

The arene moiety A may be varied to have different structures, including, but not limited to the following:

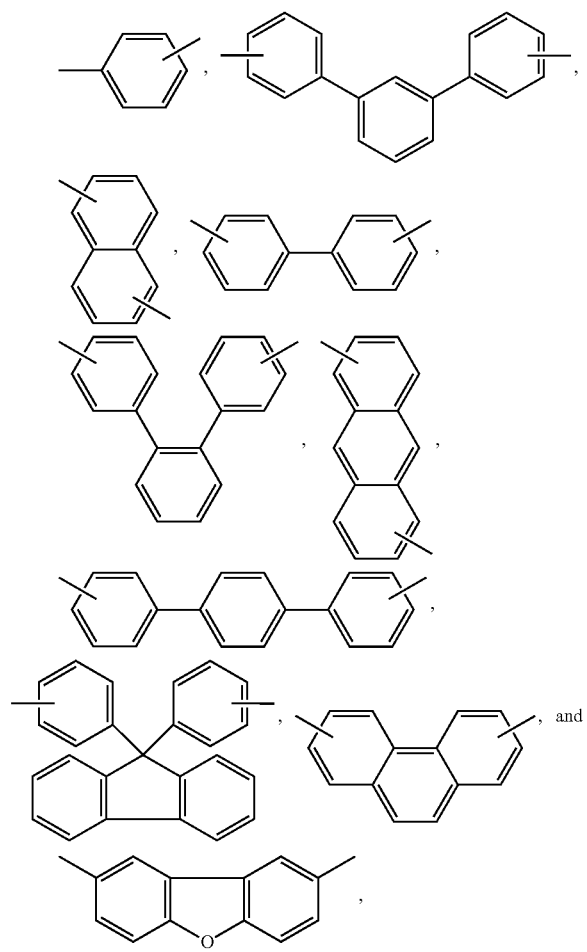

The arene moiety A is most preferably the diradical of 4,4'-biphenyl, or

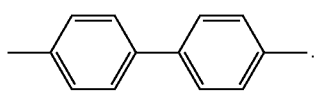

The arene moiety A may also be functionalized, if desired, using one or more functional groups such as, for example, and without limitation, sulfate, phosphate, hydroxyl, carbonyl, ester, halide, or mercapto.

The cross-linking compound can be formed, for example, by treating a halogenated arene with an alkyllithium in order to exchange the halogen with lithium, followed by the addition of 9-florenone and acid. This method of formation is described and shown in more detail in International Patent Application Publication No. WO 2013/074120 A1, which is incorporated herein by reference in relevant part concerning the method of formation.

The cross-linking composition and the organic polymer composition also contain a cross-linking reaction additive. The cross-linking reaction additive(s) include organic acids and/or acetate compounds, which can promote oligomerization of the cross-linking compound. In one embodiment, the oligomerization cat be carried out by acid catalysis using one or more organic acid(s), including glacial acetic acid, acetic acid, formic acid, lactic acid, citric acid, oxalic acid, uric acid, benzoic acid and similar compounds. An oligomerization reaction using one of the cross-linking compounds listed above is as follows:

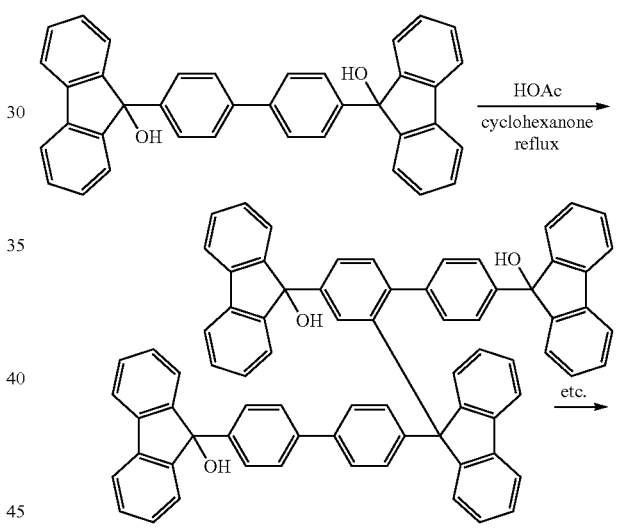

In other embodiments, inorganic acetate compounds, such as those having a structure according to formula (II) below may also be used instead of or in combination with the organic acids:

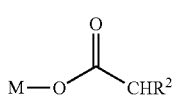

(II)

wherein M is a Group I or a Group II metal. $R^2$ in Formula (II) may preferably be an alkyl, aryl or aralkyl group. For example, $R^2$ may be a hydrocarbon group of 1 to about 30 carbon atoms, preferably 1 to about 15 carbon atoms, including normal chain and isomeric forms of methyl, ethyl, propyl, pentyl, hexyl, heptyl, octyl, nonyl, decyl, ethenyl, propenyl, butenyl, hexenyl, heptenyl, octenyl, nonenyl, decenyl, and the like. $R^2$ may also have from 0 to about 10 ester or ether groups along or in a chain of the hydrocarbon group, and preferabyl about 0 to about 5 such ester or ether groups. Suitable $R^2$ aryl and aralkyl groups, including those based on phenyl, naphthyl, and similar groups, which may each include optional lower alkyl groups on the aryl structure of from 0 to about 10 carbon atoms, preferably about 0 to about 5 carbon atoms. $R^2$ may further include 0 to about 10, preferably 0 to about 5, functional groups if desired such as sulfate, phosphate, hydroxyl, carbonyl, ester, halide, mercapto and/or potassium on the structure.

Oligomerization of the cross-linking compound with an acetate compound can afford the same resultant oligomerized cross-linking composition as achieved when adding an organic acid. The cross-linking reaction additive may be lithium acetate hydrate, sodium acetate, potassium acetate, rubidium acetate, cesium acetate, francium acetate, beryllium acetate, magnesium acetate, calcium acetate, strontium acetate, barium acetate, and/or radium acetate, and salts and derivatives thereof. More preferably, the cross-linking reaction additive is acetate hydrate, sodium acetate and/or potassium acetate, and salts and derivatives of such compounds. An oligomerization reaction using of one of the cross-linking compounds can proceed as follows:

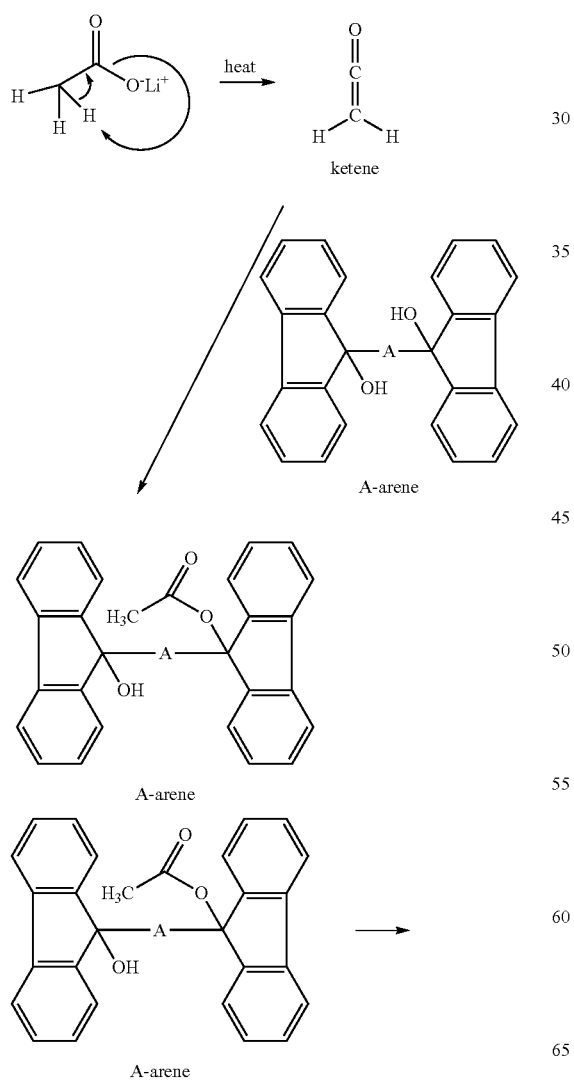

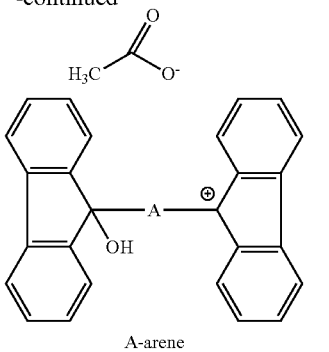

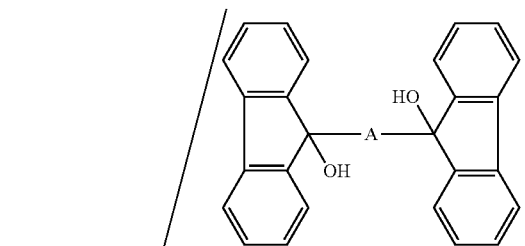

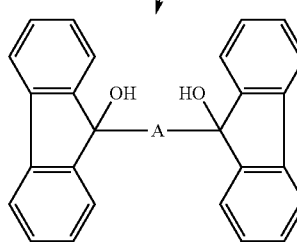

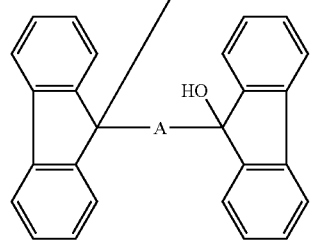

and higher oligomers

The cross-linking composition preferably has a weight percentage ratio of the cross-linking compound to the cross-linking reaction additive of about 10:1 to about 10,000:1, and more preferably about 20:1 to about 1000:1 for achieving the best results. In making the cross-linking composition, in one embodiment, the components are combined prior to addition of an organic polymer to make an organic polymer composition. Alternatively, they may all be combined simultaneously.

The amount of the cross-linking compound in the cross-linking composition is preferably about 70% by weight to about 98% by weight, more preferably about 80% by weight to about 98% by weight, and most preferably about 85% by weight to about 98% by weight based on the weight of the cross-linking composition. The amount of the cross-linking reaction additive in the cross-linking composition is preferably about 2% by weight to about 30% by weight, more preferably about 2% by weight to about 20% by weight, and most preferably about 2% by weight to about 15% by weight.

The organic polymer composition for use in forming a cross-linked polymer includes at least one organic polymer. The at least one organic polymer may be one of a number of higher glass transition temperature organic polymers, such as, but not limited to poly(arylene ether)s, polysulfones, polyethersulfones, polyimides, polyamides, polyureas, polyurethanes, polyphthalamides, polyamide-imides, poly(benzimidazole)s and polyaramids. Preferably the polymers are non-functionalized, in that they are chemically inert and they do not bear any functional groups that are detrimental to their use in down-hole tool articles of manufacture or end applications.

More preferably, the organic polymer is a poly(arylene ether) including polymer repeating units of the following structure:

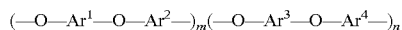

wherein $Ar^1$, $Ar^2$, $Ar^3$ and $Ar^4$ may be the same or different aryl radicals, such as those groups listed above as the arene moieties for the cross-linking compound, m=0 to 1.0, and n=1−m.

More preferably, the organic polymer is a poly(arylene ether) having a structure according to the general structure above wherein n is 0 and m is 1, with repeating units according formula (V) and having a number average molecular weight (Mn) of about 10,000 to about 30,000:

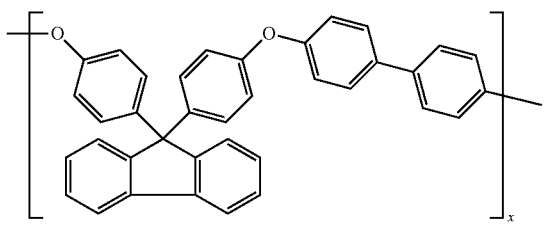

(V)

Such organic polymers may be obtained commercially for example, as Ultura™ from Greene, Tweed and Co., Inc., Kulpsville, Pa.

The organic polymer composition preferably has a weight percentage ratio of the organic polymer to the combined weight of the cross-linking compound and the cross-linking reaction additive of about 1:1 to about 100:1, and more preferably about 3:1 to about 10:1 for achieving the best results.

In making the organic polymer composition, it is preferred that the cross-linking compound and the cross-linking reaction additive components are combined prior to addition of an organic polymer to make an organic polymer composition. Alternatively, they may all be combined simultaneously.

The amount of the cross-linking compound in the organic polymer composition is preferably about 1% by weight to about 50% by weight, more preferably about 5% by weight to about 30% by weight, and most preferably about 8% by weight to about 24% by weight based on the total weight of an unfilled organic composition including the cross-linking compound, the cross-linking reaction additive and the organic polymer.

The amount of the cross-linking reaction additive in the organic polymer composition is preferably about 0.01% by weight to about 33% by weight, more preferably about 0.1% by weight to about 10% by weight, and most preferably about 0.2% by weight to about 2% by weight based on the total weight of an unfilled organic polymer composition including the cross-linking compound, the cross-linking reaction additive and the organic polymer.

The amount of the organic polymer in the organic polymer composition is preferably about 50% by weight to about 99% by weight, more preferably about 70% by weight to about 95% by weight, and most preferably about 75% by weight to about 90% by weight based on the total weight of an unfilled organic polymer composition including the cross-linking compound, the cross-linking reaction additive and the organic polymer.

The organic polymer composition may further be filled and/or reinforced and include one or more additives to improve the modulus, impact strength, dimensional stability, heat resistance and electrical properties of composites and other finished articles of manufacture formed using the polymer composition. These additive(s) can be any suitable or useful additives known in the art or to be developed, including without limitation continuous or discontinuous, long or short, reinforcing fibers such as, for example, carbon fiber, glass fiber, woven glass fiber, woven carbon fiber, aramid fiber, boron fiber, PTFE fiber, ceramic fiber, polyamide fiber and the like; and/or one or more fillers such as, for example, carbon black, silicate, fiberglass, calcium sulfate, boron, ceramic, polyamide, asbestos, fluorographite, aluminum hydroxide, barium sulfate, calcium carbonate, magnesium carbonate, silica, alumina, aluminum nitride, borax (sodium borate), activated carbon, pearlite, zinc terephthalate, graphite, talc, mica, silicon carbide whiskers or platelets, nanofillers, molybdenum disulfide, fluoropolymer fillers, carbon nanotubes and fullerene tubes. Preferably, the additive(s) include reinforcing fiber such as continuous or discontinuous, long or short, carbon fiber, PTFE fiber, and/or glass fiber.

In making the organic polymer composition, it is preferred that the additive(s) is/are added to the composition along with or at about the same time that the oligomerized cross-linking composition (or the combined components thereof) is combined with the organic polymer to make an organic polymer composition, however, the manner of providing reinforcing fibers or other fillers may be according to various techniques for incorporating such materials and should not be considered to limit the scope of the invention. The amount of additives is preferably about 0.5% by weight to about 65% by weight based on the weight of the organic polymer composition, and more preferably about 5.0% by weight to about 40% by weight.

In addition, the organic polymer composition may further comprise other compounding ingredients, including stabilizers, flame retardants, pigments, plasticizers, surfactants, and/or dispersants such as those known or to be developed in the art to aid in the manufacturing process. In making the organic polymer composition, it is preferred that the one or more fillers is/are added to the organic polymer composition along with or at about the same time that the oligomerized crosslinking composition (or the combined components thereof) is combined with the organic polymer to make an organic polymer composition, however, as noted above, the manner of providing such materials may be according to various techniques and should not be considered to limit the scope of the invention. The amount of the compounding ingredients that can be combined into the organic polymer composition, if used, is preferably about 5% by weight to about 60% by weight of a total of such ingredients based on the weight of the organic polymer composition, more preferably about 10% by weight to about 40% by weight, and most preferably about 30% by weight to about 40% by weight.

In an embodiment of the method of the invention, after providing, for example by manufacturing, a cross-linking composition as described herein, the cross-linking composition is heated to induce oligomerization of the cross-linking compound as shown in Examples 1 and 4. In one embodiment of the method, the oligomerization occurs by acid catalysis. Acid catalysis is used when an organic acid is employed as the cross-linking additive. The $R^1$ functionality of the cross-linking compound of Formula (IV) is dissociated from the remainder of the compound to afford a carbocation which then can undergo a Friedel-Crafts alkylation the organic polymer, resulting in bond formation. In another embodiment of the method of the present invention, oligomerization of the cross-linking compound may occur by doping. Doping is accomplished by physically mixing solid form reactants in the composition at lower temperatures of about −100° C. to about −300° C. prior to reacting the overall composition for curing and/or heat molding the resulting composition to form an article.

The method may further comprise adding the reacted oligomerized cross-linking composition to an organic polymer to form a cross-linkable composition as demonstrated in Examples 2 and 5. The unmodified cross-linking compound may be added directly to the organic polymer and blended with the cross-linking reaction additive to simultaneously oligomerize and bind to the organic polymer as demonstrated in Example 3. Once the reactive oligomerized cross-linking compound reacts with the organic polymer, the rate of cross-linking of the organic polymer occurs at a later time in the curing process as compared to the rate of cross-linking that would occur in an organic polymer composition having a prior art cross-linking composition using the same crosslinking compound but without the cross-linking reaction additive. The result is complete filling of the mold and a more excellent end heat molded/extruded, etc. product formed from the composite polymer during various heat molding techniques (See FIGS. 4A and 4B which show the difference in a finished part formed without and with, respectively, a crosslinking reactive additive).

Figure 4A:
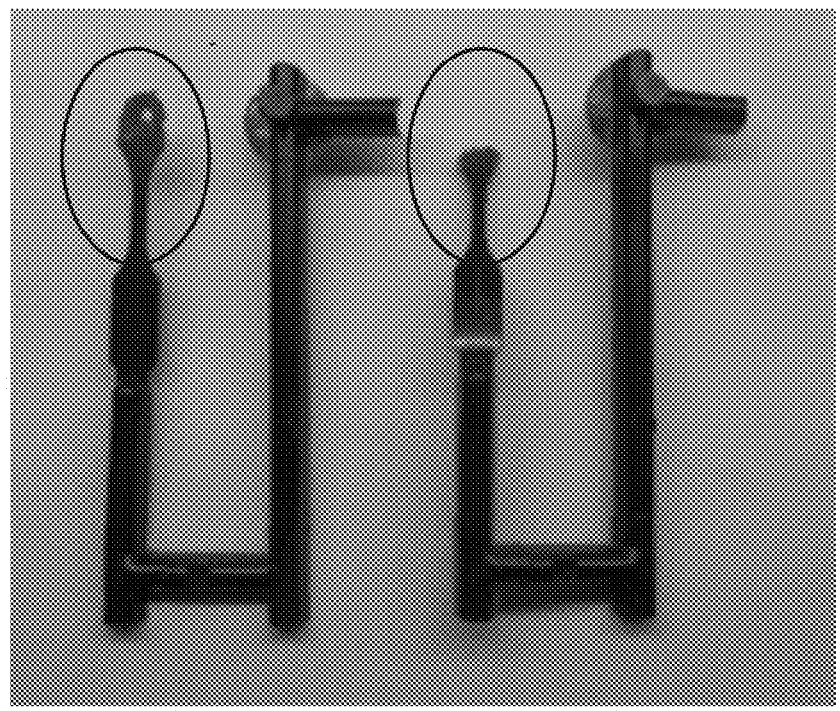
FIG. 4A is a photographic representation of an injection-molded articles of manufacture of a molded organic polymer composition containing a non-oligomerized cross-linking compound.
Figure 4B:
FIG. 4B is a photographic representation of injection-molded articles of manufacture of a molded organic polymer composition containing with an oligomerized cross-linking compound.

Powders of the organic polymer compositions of the present invention were made into pellets, and the pellets were subjected to a heat molding process. Heat molding of the organic polymer compositions can be accomplished by many different means already known or to be developed in the art, including extrusion, injection molding, compression molding and/or injection/compression molding. As shown in FIG. 4B, pellets of an organic polymer composition of the present invention were injection molded on an Arbug® 38-ton injection molding machine with a cold runner system that includes a hot sprue. Bars made with a prior art unmodified cross-linking compound as shown in FIG. 4A were not able to be completely filled, even with 36,000 psi fill pressure. However, bars made with the reactive oligomerized cross-linking intermediate compounds of the present invention were able to be processed and completely filled with only 26,000 psi fill pressure.

Heat molding to form an article of manufacture may be accomplished by any method known or to be developed in the art including but not limited to heat cure, cure by application of high energy, heat cure, press cure, steam cure, a pressure cure, an e-beam cure or cure by any combination of means, etc. Post-cure treatments as are known in the art or to be developed may also be applied, if desired. The organic polymer compositions of the present invention are cured by exposing the composition to temperatures greater than about 250° C. to about 500° C., and more preferably about 350° C. to about 450° C.

The compositions and/or the methods described above may be used in or to prepare articles of manufacture of downhole tools and applications used in the petrochemical industry. Particularly, the article of manufacture is selected from the group consisting of acid-resistant coatings, chemical-casted films, extruded films, solvent-casted films, blown films, encapsulated products, insulation, packaging, composite cells, connectors, and sealing assemblies in the shape of O-rings, V-rings, U-cups, gaskets, bearings, valve seats, adapters, wiper rings, chevron back-up rings, and tubing.

The above embodiments of invention will now be described in accordance with the following, non-limiting examples:

EXAMPLE 1

Preparation of a Cross-Linking Composition Using an Organic Acid Cross-Linking Additive. A 15.34 g portion of the cross-linking compound identified as Diol-2 in Examples 2 and 4 of International Patent Application Publication No. WO 2013/074120 A1 was dissolved in a mixture of 20 mL of glacial acetic acid and 300 mL of cyclohexanone. The solution was heated to reflux for a total of 13.5 hours, after which the glacial acetic acid and cyclohexanone were removed via atmospheric distillation. The product was a pasty solid residue, 1H and 13C NUR data indicates a 1:00:1:00 molar ratio of C—OH to the cardo carbon of the cross-linking compound.

EXAMPLE 2

Preparation of an Organic Polymer Composition after Oligomerization of the Cross-Linking Compound Using an Organic Acid Cross-Linking Additive. A 0.85 g portion of the residue of Example 1 was combined with 9.15 g of 5000FP Polyether ether ketone (PEEK) powder. Analysis was conducted by an AR2000 Rheometer with 8 mm parallel plates and an inert nitrogen purge to determine the rate of cure. Samples were loaded and stabilized for 4.5 minutes at 380° C., and 60-minute time sweep tests were performed to record the change in the modulus to determine the rate of cure for 50 minutes. The results are shown in FIG. 1.

EXAMPLE 3

Figure 2:
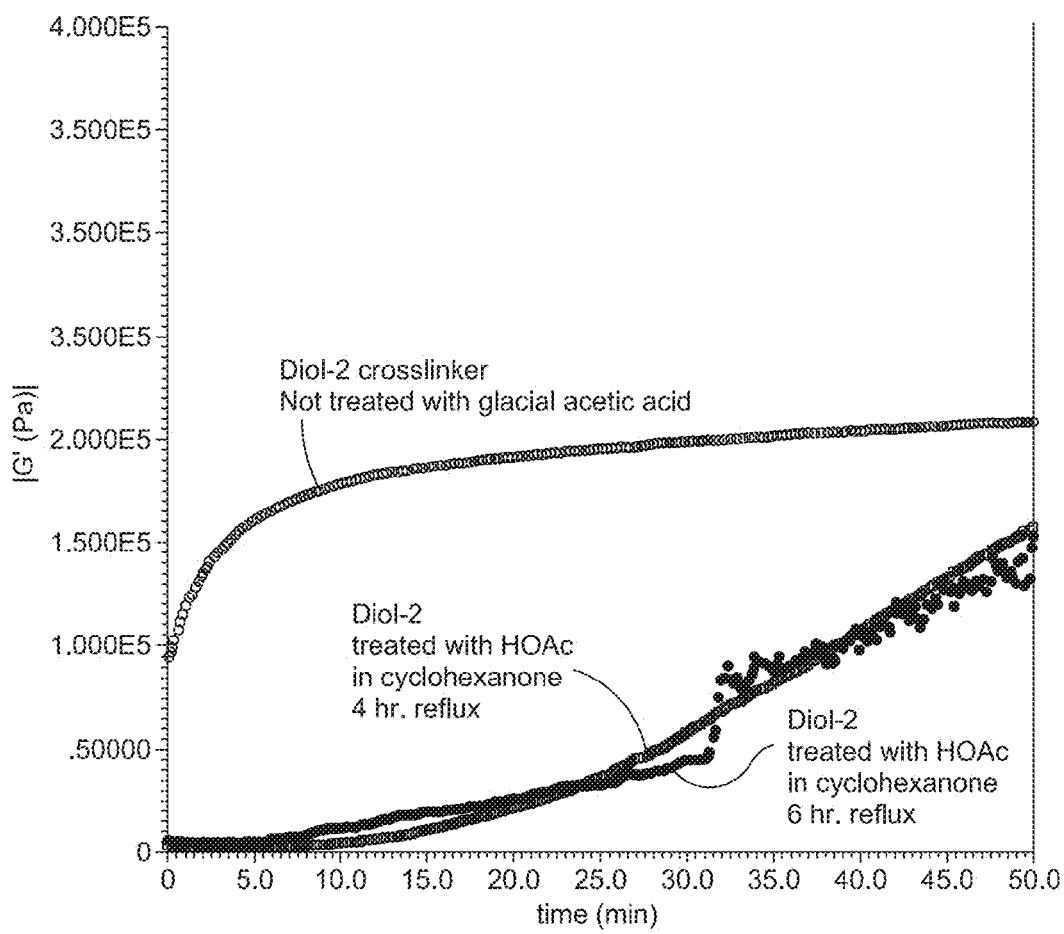
FIG. 2 is a is a graphical representation of the thermal rate of cure of an organic polymer composition after combination with a cross-linking compound and an organic acid.
Figure 2A:
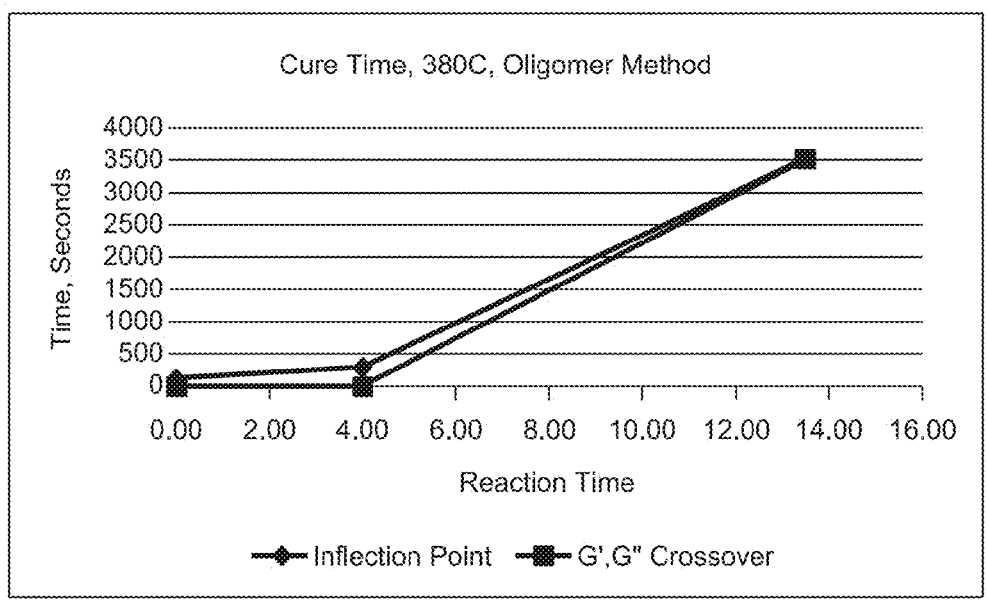
FIG. 2A is graphical representation of the cure times versus the oligomerization reaction times in 5000FP Blends of organic polymer compositions.

Preparation of an Organic Polymer Composition During Oligomerization of the Cross-Linking Compound Using an Organic Acid Cross-Linking Additive. 13.725 g of 5000FB Polyether ether ketone (PEEK) powder was combined with 1.275 g of the above-noted cross-linking compound Diol-2, 100 mL cyclohexanone, and 20 mL glacial acetic acid in a 500 ml RBF equipped with a magnetic stir bar. After 4 hours reflux time, the glacial acetic acid and cyclohexanone were removed using a short path still, followed by drying in a vacuum oven at 120 for 20 hours. Analysis was conducted by an AR2000 Rheometer with 8 mm parallel plates and an inert nitrogen purge to determine the rate of cure. Samples were loaded and stabilized for 4.5 minutes at 380° C., and 60-minute time sweep tests were performed to record the change in the modulus to determine the rate of cure for 50 minutes. The results are summarized in Table 1 and shown in FIGS. 2 and 2A.

TABLE 1

| Sample % | cross-linker | Reaction time, hrs | Cross Over (G' = G''), sec | Inflection Point, sec |
|---|---|---|---|---|
| Control 8% |  | 0.00 | 0 | 128 |
| Example 3 | 8% | 4.00 | 0 | 298 |
| Example 2 | 8% | 13.50 | 3500 | 3500 |

EXAMPLE 4

Preparation of a Cross-Linking Composition Using an Acetate Compound Cross-Linking Additive. Four blends of the cross-linking compound Diol-2 identified above and lithium acetate dehydrate were prepared using a Spex® 6870 freezer mill. Samples were cooled in liquid nitrogen at approximately −195° C. for 15 min., then ground for 12 cycles for 3 min., followed by 5 minutes of cooling for a total of 96 min. grinding time at −196° C. at a speed of 10 cycles/s. No solvents were used in this Example. The weight amounts of each component of the composition is listed in Table 2 below:

TABLE 2

| Blend # | Mass of lithium acetate dehydrate | Mass of Diol-2 | % lithium acetate dihydrate in Diol-2 |
|---|---|---|---|
| 1 | 0.225 g | 9.775 g | 0.225 |
| 2 | 0.45 g | 9.55 g | 0.45 |

TABLE 2-continued

| Blend # | Mass of lithium acetate dehydrate | Mass of Diol-2 | % lithium acetate dihydrate in Diol-2 |
|---|---|---|---|
| 3 | 0.90 g | 9.10 g | 0.90 |
| 4 | 0.317 g | 0.8 g | 28.4 |

EXAMPLE 5

Figure 3:
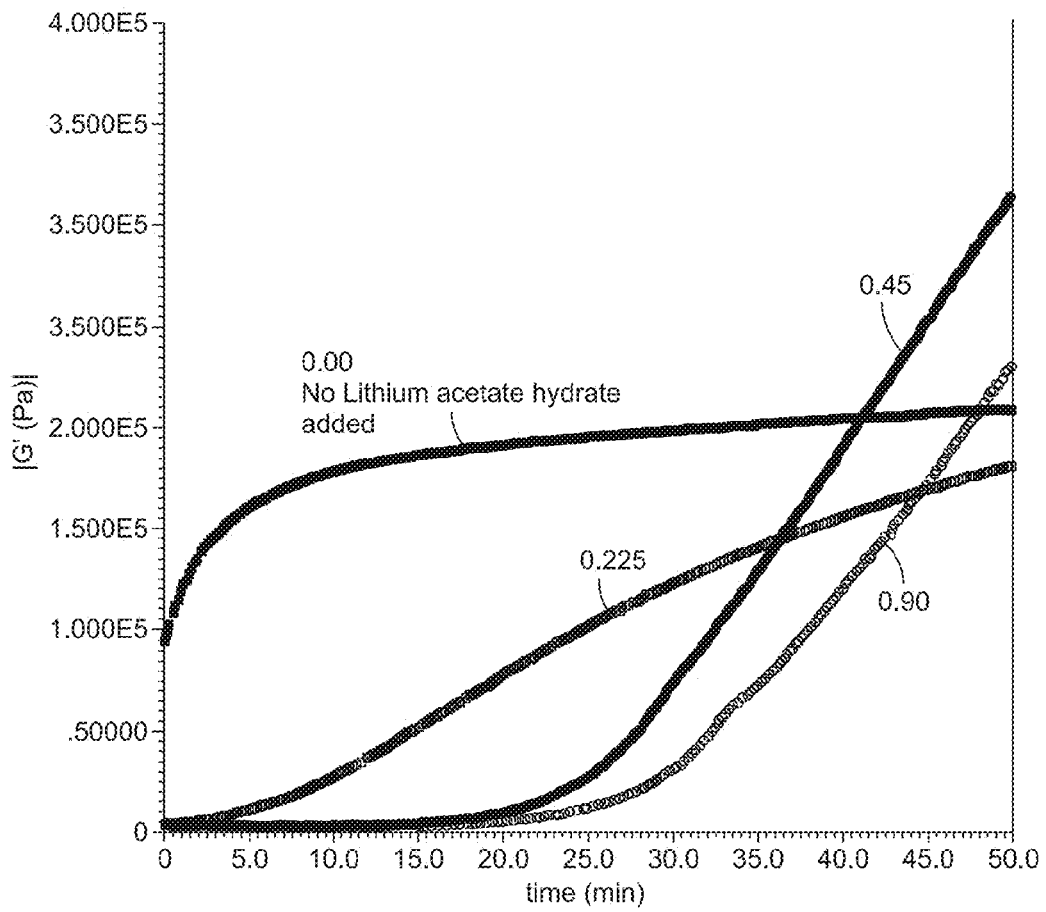
FIG. 3 is a is a graphical representation of the thermal rate of cure of an organic polymer composition after combination with a cross-linking compound and an acetate compound.
Figure 3A:
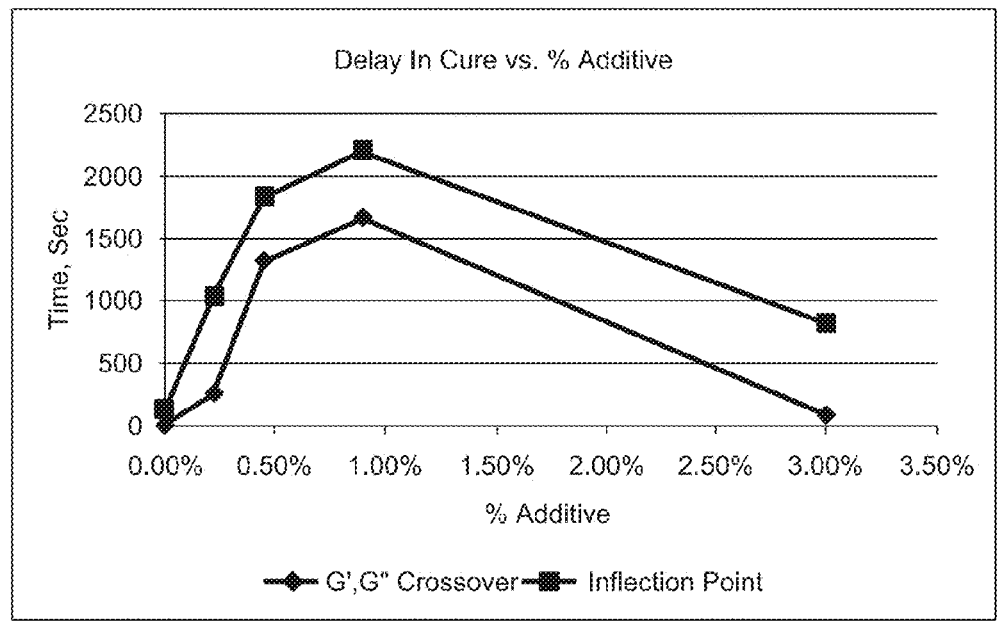
FIG. 3A is a graphical representation of the controlled thermal rate of cure that correlates with the percent of oligomerized cross-linking compound that has been added to an organic polymer composition.

Preparation of an Organic Polymer Composition after Oligomerization of the Cross-Linking Compound Using an Acetate Compound Cross-Linking Additive. An 8.0 g portion of the oligomerized cross-linker composition of Blend 2 in Example 4 was combined with 92 g of 5000FP Polyether ether ketone (PEEK) powder in a 500 mL bottle and was shaken at 45 rpm for 30 minutes. Analysis was conducted by an AR2000 Rheometer with 8 mm parallel plates and an inert nitrogen purge to determine the rate of cure. Samples were loaded and stabilized for 4.5 minutes at 380° C., and 60-minute time sweep tests were performed to record the change in the modulus to determine the rate of cure for 50 minutes. The results are summarized in Table 3 and in FIGS. 3 and 3A.

TABLE 3

| Sample | % cross-linker | % Additive | Cross Over (G' = G''), sec | Inflection Point, sec |
|---|---|---|---|---|
| Control | 8% | 0.0000% | 0 | 128 |
| Blend 1 | 8% | 0.2250% | 256 | 1036 |
| Blend 2 | 8% | 0.4500% | 1317 | 1836 |
| Blend 3 | 8% | 0.9000% | 1665 | 2203 |
| Blend 4 | 8% | 3.0000% | 88 | 818 |

The Applicant has also discovered that part of the lack of control and fast cure of compositions of crosslinkable organic polymers, particularly those having aromatic groups in the backbone chain, and including those having rate-controlling additives as noted above, is the presence of reactive end groups, particularly those having halogen-containing reactive groups, such as bromine-containing reactive end groups. An example of a cross-linked polyarylene ether polymer having a halogen-containing reactive end group, in this instance, a bromine-containing end group which is a bi-phenyl bromide group is shown below in formula (III):

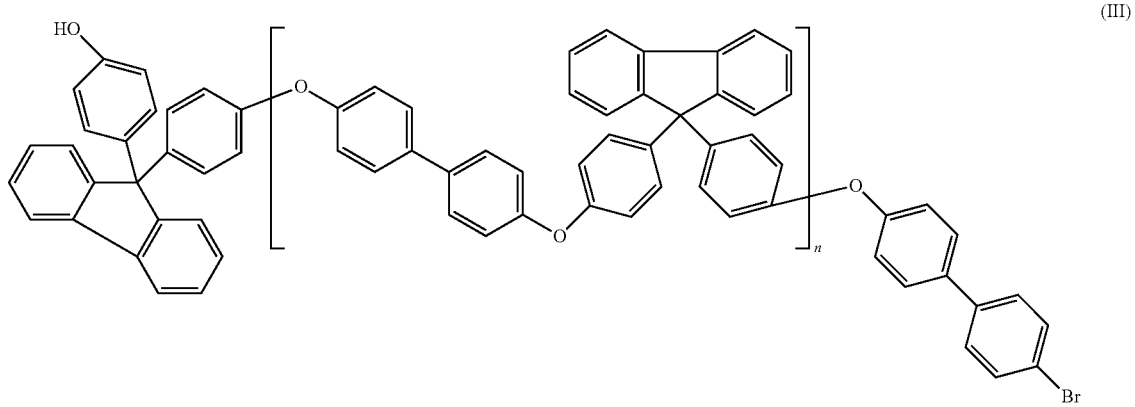

(III)

Such end groups can negatively impact processing and properties of cross-linked organic polymers. The treatment of such polymers, which are typically formed using a compound for cross-linking, to remove of such end groups results in a material that is significantly more processable than the same polymer without such treatment.

Typical synthesis procedures yield number average molecular weights (Mn) of about 20,000 to about 25,000 daltons, and a repeat unit of a polymer such as that shown in formula III would have about 502 daltons. Thus, there would be about 46 repeat units in a polymer of a number average molecular weight of 24,000 in a given batch. Each polymer chain has at least two end groups. As the polymer is a condensation polymer, there is roughly a 50% chance of a halogen-containing end group, such as the bromine-containing group, biphenyl bromine end group as shown in formula III above, being present. Thus, each such polymer is expected to have about one of the bromine-containing end groups per chain, corresponding to an approximate bromine level of about 3,100 to 4,000 ppm for polymers having a single bromine end group. If the polymer incorporates two such end groups, the bromine level could be as much as 6,200 to about 8,000 ppm bromine. The applicants did a bromine analysis of a typical polymer in this category having a number average molecular weight of 25,300 which yielded a bromine level of 3,400 ppm, which was within theoretical predictions.

The biphenyl bromine end group and other similar end groups is/are not expected to be as thermally stable as the aromatic cross-linked backbone and thus may be thermally cleaved during processing at high temperatures (of about 350° C. to about 400° C.). For example, the phenyl-bromine bond is known in the art to be weak, and the bromine radical very reactive. Thus, heating of brominated aromatics at high temperatures can result in the phenyl-bromine bond breaking to produce a bromine radical and a phenyl radical. See, Ladacki et al., Proceedings of the Royal Society of London: Series A. Mathematical and Physical Sciences, (1953) 219, 11, pp. 341-352, "Studies of the Variations in Bond Dissociation Energies of Aromatic Compounds, I. Monobromoaryles." The bromine radical, as with other halogens, being extremely reactive, will rapidly abstract a proton to produce HX (wherein X is a halogen) as a byproduct. With respect to bromine, HBr forms and is an acid which is known to react with hydroxyl groups of 3° trityl alcohols to form carbocations via an acid-base reaction and to form tritylbromide, which is the conjugate acid of the trityl alcohol, and water. The Applicant herein observed that the hydroxyl groups of 9,9'-(biphenyl-4,4'-diyl)bis(9H-fluoren-9-ol) behave very similarly to trityl alcohol in this regard. Thus, the resulting HBr acts as an initiator and will then generate a reactive carbocation which thus accelerates cross-linking (see reaction scheme shown in (A) below). This behavior can partly counteract the degree of control provided by the reactive cross-linking additives described above that inhibit reaction rate, and further, may speed up cross-linking.

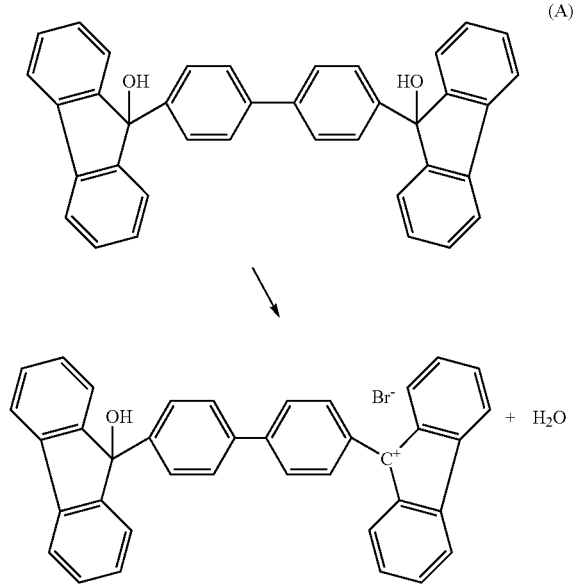 [SMILES: OC1(c2ccc(-c3ccc(C4(O)c5ccccc5-c5ccccc54)cc3)cc2)c2ccccc2-c2ccccc21 ; OC1(c2ccc(-c3ccc([C+]4c5ccccc5-c5ccccc54)cc3)cc2)c2ccccc2-c2ccccc21 ; [Br-] ; O]

A thermally produced carbocation generated by the loss of the hydroxyl group of 9,9'-(biphenyl-4,4'-diyl)bis(9H-fluoren-9-ol) becomes a reactive intermediate and likely a rate-limiting step in initiation of a cross-linking reaction. A proposed reaction mechanism (B) for the cross-linking reaction of an organic polymer using 9,9'-(biphenyl-4,4-diyl)bi(9H-fluoren-9-ol) and related variants is shown below.

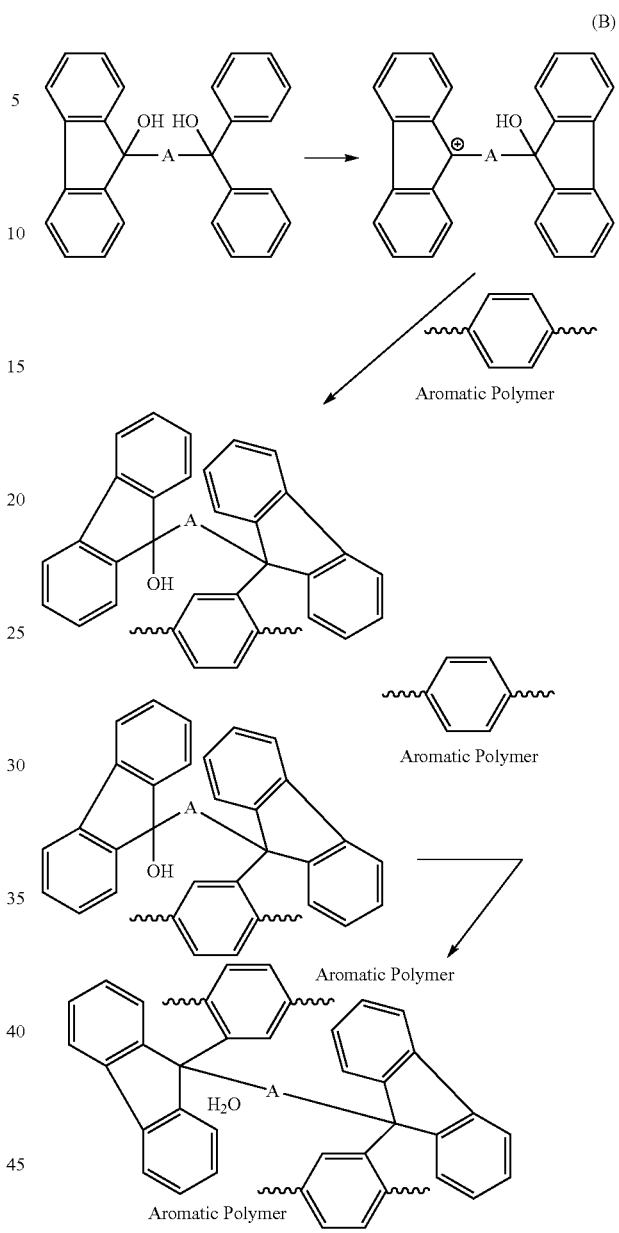

Lithium acetate and similar compounds as described hereinabove act as basic inhibitors to moderate the thermal activation of the phenylfluorenol end groups and to inhibit formation of a reactive carbocation. However, in such a reaction scheme, acidic HBr or other similar halogen acids generated through thermal decomposition of the cross-linked polymer end groups, for example, can react with the basic acetate anion to neutralize it, thus at the same time neutralizing the inhibiting effect of the reactive additive.

Continuing this evaluation using the lithium acetate as the prospective reactive additive for controlling reaction rate of the cross-linking reaction, the theoretical molar quantity of HBr or other similar acid that may be generated is approximately 2.4 times higher than the molar quantity of lithium acetate dihydrate (base) added as the inhibiting reaction additive. Thus, the instinctual path to overcome this issue would be to incorporate high concentrations of lithium acetate or other reactive additives with inhibiting effect to neutralize the acid being generated. Unfortunately, when too much excess and/or higher amounts of such inhibiting reactive additives, e.g., lithium acetate, are used, it can contribute to a contrary effect in the presence of the halogen acid as the excess additive may actually begin to accelerate the reaction, thus limiting the range of effectiveness of the additives noted in the invention described above in a complex reaction mechanism.

In addition to issues impacting reaction rate aside from generation of a halogen acid, such as HBr, the product of a thermal dehydrohalogenation reaction during cross-linking may create a very reactive aryl radical or benzyne intermediate. The reactive aryl intermediate generated by thermally-induced dehydrohalogenation could itself act as a thermally activated cross-link site and is difficult to control due to the exothermic nature of reactions such as those between 9,9'-(biphenyl-4,4'-diyl)bis(9H-fluoren-9-ol) and a crosslinking organic polymer such as a polyarylene ether, which exothermic reaction profile can be observed and evaluated via Differential Scanning calorimetry (DSC). The exothermic curves can be used to estimate half-lives of exothermic reactions via the Borchardt and Daniels Method. See, ASTM-E2041, Standard Test Method for Estimating Kinetic Parameters by Differential Scanning Calorimeter Using the Borchardt and Daniels Method. This method allows calculation of activation energies and other kinetic parameters. Once these rate coefficients are obtained, reaction half lives at various temperatures can be calculated. The half lives obtained for various treatments of polymers and inhibitors can then be compared to estimate the improvement in cure time (cross-linking reaction time) gained by specific treatments.

With the foregoing information in mind, the Applicant herein discovered that contrary to the above problematic approaches, it is possible to chemically remove the halogen from a halogen-containing end group but to control the halogen-containing byproducts and enable formation of purified organic polymers, in the sense that such polymers are dehalogenated prior to cross-linking. Such dehalogenated, purified organic polymers are then capable of being easily cross-linked and molded, so that there is a slower and more compatible, controlled cross-linking reaction during molding, and traditional heat-molding techniques may be readily used.

Cross-linked articles formed from cross-linking the dehalogenated organic polymers using a cross-linking compound and optionally one or more reactive cross-linking additives according to the invention described herein, as well as organic polymer compositions having a dehalogenated organic polymer and a cross-linking compound for use in forming a cross-linked organic polymer. In addition, methods for preparing such compositions and polymers, and articles of manufacture formed from the aforementioned compositions and by such methods are within the invention and are useful in extreme condition end applications such as in down-hole applications.

Cross-linking compositions containing a cross-linking compound(s) can be reacted to form a reactive oligomerized cross-linking intermediate either in situ during thermal molding in combination with a cross-linkable dehalogenated organic polymer, and/or by reacting a separate cross-linking composition having a cross-linking compound(s) and a cross-linking reaction additive(s) to form the oligomerized cross-linking intermediate and then combining the oligomerized cross-linking intermediate with a cross-linkable dehalogenated organic polymer and heating and molding the combined materials to form an article. The intermediate oligomer reaction product of the cross-linking compound(s) with the optional crosslinking reaction additive(s) act as inhibitors and enable control of a cross-linking reaction when combined with an organic polymer generally, particularly those with aromatic groups in the backbone, but can enable even lower rates of thermal cure and allow a broader window and better control and reaction rate inhibition during heat mold when a dehalogenated organic polymer is used as a base polymer.

Figure 7:
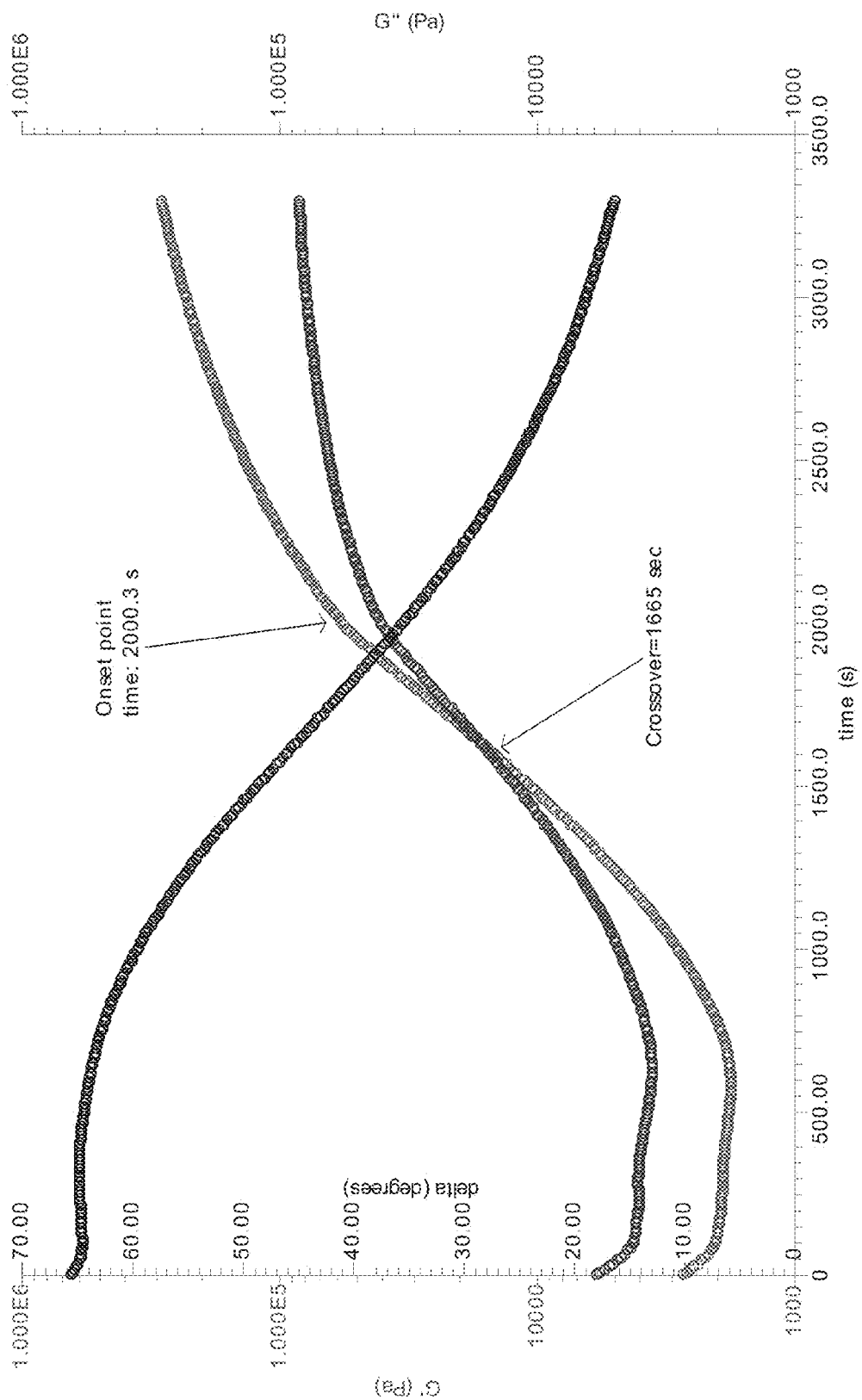
FIG. 7 is a prior art graph from Parallel Plate Rheology of Blend 3, at 380° C., referenced to J. Mercel et al., "Thermal Analysis of Polymers: Fundamentals and Applications," p. 445, Wiley, ed. 1 (2009).

As noted above, formation of cross-links in an organic polymer cross-linking to itself or in an organic polymer composition comprising an unmodified cross-linking compound may be completed within about 2 minutes at about 380° C., the typical processing temperature of polyetherether ketone (PEEK) (FIG. 7).

Utilization of one or more cross-linking reaction additive(s) has been identified to help provide polymers with high glass transition temperatures and high cross-link density cure more stably when combined with a cross-linking compound such as that of formula (IV). Polymers with high thermal stability of up to 500° C. and high crosslink density, while desirable, as mentioned above, display a very high melt viscosity before further processing, and thus are very difficult to melt process. If the rate of cross-linking is not controlled before molding of a composition into a final article, the article of manufacture may begin to prematurely cure before or during heat molding or proceed too rapidly causing incomplete mold fill, equipment damage, and inferior properties in the article. Thus, the invention is also directed to improving by controlling or inhibiting the rate of cross-link formation in an organic polymer using the cross-linking compound(s) and/or the cross-linking reaction additive(s) as described above in combination with a dehalogenated organic polymer, such as a debrominated organic polymer, which is capable of cross-linking. This provides a reaction wherein the inhibitor(s) (not impeded by X or HX formation, such as B or HBr) can work more effectively and delay the onset of cross-linking in the organic polymer for as much as several minutes beyond what is achieved without the dehalogenation treatment of the initial polymer to allow for rapid processing and shaping of the resultant organic polymer structures in a controlled manner.

In the organic polymer compositions herein for use in forming a cross-linked organic polymer, the composition includes at least one organic polymer that is dehalogenated. Polymers which can benefit in a preferred manner by a dehalogenation treatment prior to crosslinking in include at least one organic polymer that may be one of a number of higher glass transition temperature organic polymers and/or which have an aromatic group in the backbone of the polymer, including, but not limited to, for example, poly(arylene ether)s, polysulfones, polyethersulfones, polyimides, polyamides, polyureas, polyurethanes, polyphthalamides, polyamideimides, poly(benzimidazole)s and polyaramids. Preferably the polymers are non-functionalized, in that they are chemically inert and they do not bear any functional groups that are detrimental to their use in down-hole tool articles of manufacture or end applications. Such polymers if able to benefit from a dehalogenation treatment prior to cross-linking would also have at least one halogen-containing reactive group. Generally such groups, as discussed above, are generally terminal groups which may remain from the polymerization process or other end-capping reactions and the like.

More preferably, in one embodiment herein, the organic polymer is a poly(arylene ether) such as those noted above including polymer repeating units in the backbone of the polymer chain having the following structure:

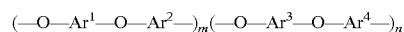

wherein $Ar^1$, $Ar^2$, $Ar^3$ and $Ar^4$ may be the same or different aryl radicals, such as those groups listed above as the arene moieties for the cross-linking compound, m=0 to 1.0, and n=1−m.

More preferably, the organic polymer is a poly(arylene ether) having a structure according to the general structure above wherein n is 0 and m is 1, with repeating units according to formula (V) and having a number average molecular weight (Mn) of about 10,000 to about 30,000:

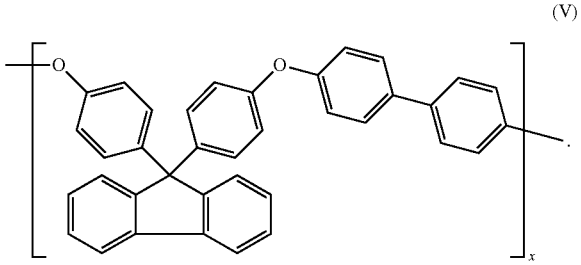

As noted above, such organic polymers may be obtained commercially for example, as Ultura™ from Greene, Tweed and Co., Inc., Kulpsville, Pa.

Other suitable organic polymers for use in the invention as noted above, such as polyarylenes and polyarylene ethers, may be made with, for example, diiodobiphenyl monomer and/or dibromobiphenyl monomers. In such instances, the method used herein should be used to remove the bromine-containing or iodine-containing reactive groups to deiodinate or debrominate the polymer. For other suitable polymers, such as polysulfones, many are formed using chlorinated monomers in synthesis which may leave chlorine-containing reactive groups, and the method herein should be used to dechlorinate the chlorine-containing reactive groups. Thus, it should be understood to one skilled in the art, that for organic polymers having halogen-containing reactive groups that are present from formation by a polymerization process leaving reactive, halogen-containing groups, such as halogen-containing end groups, such organic polymers can be dehalogenated to provide purified organic polymers for use in cross-linking reactions where rate control is an issue in employing such polymers in traditional heat molding processes.

To dehalogenate the organic polymer, an organic polymer(s) alone or in combination may be subjected to the method of the present invention. The method provides a dehalogenated organic polymer which works in the cross-linking composition to control the cross-linking reaction rate of an organic polymer having at least one halogen-containing reactive group during a cross-linking reaction. In the method, an organic polymer having a halogen-containing reactive group, such as those noted above, and preferably having one or two halogen-containing terminal groups, such as bromine, iodine, chlorine and the like, is used.

The polymer having the halogen-containing reactive group is reacted with an alkali metal compound to break the bond that connected the halogen atom to the polymer, that is, the bond between the organic polymer having the at least one halogen-containing reactive group and the halogen atom in the at least one halogen-containing reactive group. This reaction forms an intermediate having a carbocation.

The at least one halogen-containing reactive group is typically a halogen atom (X) but more often the halogen atom links to the chain, and most typically in a terminal position, by a final organic group off of the primary backbone. Such a reactive group may be represented as —$R^4$—$(X)_p$, wherein $R^4$ is carbon or a branched or straight chain organic group selected from alkyl, alkenyl, aryl and aralkyl groups of from 1 to about 30 carbon atoms, preferably 1 to about 20 carbon atoms, having from 0 to about 10 ester or ether groups, preferably 0 to about 5 such ether or ester groups along or in a chain or structure of the group, and wherein $R^4$ may be substituted or unsubstituted. Suitable alkyls include methyl, ethyl, propyl, iso-propyl, butyl, iso-butyl, tert-butyl, pentyl, heptyl and the like. Suitable alkenyls include methenyl, ethenyl, propenyl, iso-propenyl, butenyl, iso-butenyl, tert-butenyl, pentenyl, and the like. Aryl groups may be single or multiple ring structures, such as benzyl, phenyl, xylyl, biphenyl, dibenzyl, and the like, and such groups may be modified to have aryl or aralkyl groups or side chains and to form aralkyl structures as well. X represents a halogen, bromine, iodine, chlorine, flourine, and the like, and p is an integer which is 1 or 2.

The reaction of the organic polymer having the halogen-containing reactive group preferably occurs with an alkali metal compound. The alkali metal compound may be represented by $R^3$—M', wherein M' is an alkali metal and $R^3$ may be H or a branched or straight chain organic group selected from alkyl, alkenyl, aryl and aralkyl groups of from 1 to about 30 carbon atoms, preferably about 1 to about 15 carbon atoms, having from 0 to about 10 ester or ether groups, preferably 0 to about 5 such groups, along or in a chain or structure of the group. $R^3$ may be a substituted or unsubstituted group. The substituted groups may include functional groups for providing other properties to the resulting polymer, provided they do not affect the dehalogenated organic polymer ultimately formed from the process and/or do not impact the reaction or rate thereof of the organic polymer having the halogen-containing reactive halogen group or negatively impact the reaction between such polymer with the alkali metal, such functional groups may include, for example, hydroxyl, carbonyl, ester, halide, mercapto and/or potassium.

Suitable alkali metal compounds include methyl lithium, methenyl lithium, ethyl lithium, ethenyl lithium, isoproypl lithium, propyl lithium, propenyl lithium, butyl lithium, isobutyl lithium, t-butyl lithium, s-butyl lithium, n-butyl lithium, butenyl lithium, and similar compounds, methyl sodium, methenyl sodium, ethyl sodium, ethenyl sodium, isopropyl sodium, propyl sodium, propenyl sodium, n-butyl sodium, s-butyl sodium, t-butyl sodium, butenyl sodium, and similar compounds, methyl potassium, methenyl potassium, ethyl potassium, ethenyl potassium, propenyl potassium, butyl potassium, isobutyl potassium, n-butyl potassium, s-butyl potassium, t-butyl potassium, butenyl potassium, and similar compounds, as well as, for example, benzyl lithium, phenyl lithium, benzyl sodium, phenyl sodium, benzyl potassium, phenyl potassium, and other related compound. Preferably, the alkali metal compound is butyl lithium, t-butyl-lithium, butyl sodium, t-butyl sodium, butyl potassium or t-butyl potassium.

The organic polymer having the at least one halogen-containing end group is reacted with the alkali metal compound preferably in a solvent environment. The solvent is preferably capable of dissolving the organic polymer having the at least one halogen-containing reactive group but free of functional groups that react with the halogen in the halogen-containing reactive group under the reaction conditions used. Suitable solvents include, but are not limited to heptane, hexane, tetrahydrofuran, and diphenyl ether as well as similar solvents and derivatives or functionalized variants of such solvents, with the most preferred solvent being tetrahydrofuran (THF).

The reaction preferably occurs at low temperatures of less than about −20° C., preferably less than about −50° C., and more preferably less than about −70° C. so as to minimize potential side reaction between the solvent used and the alkali metal compound. For example, as the half life of t-butyl-lithium THF at −20° C. is about 42 minutes, by reacting it below that temperature, for example, at −70° C. to −78° C., further time is provided, as the estimated half life of that compound in THF is about 1300 minutes. Thus the reaction proceeds as desired and reactive interference by thermal issues is minimized. The reaction preferably proceeds until a majority of halogen atoms are removed from the organic polymer, preferably substantially all of the halogen atoms, and most preferably virtually all or all of the halogen atoms are removed. Reaction times will vary depending on the solvent used, the alkali metal compound and the temperature of the reaction, hut is expected to continue for about 0.5 to about 4 hours, and preferably about 1 to about 2 hours.

Before introducing the organic polymer to such a solvent reaction, it is preferred that the organic polymer having the at least one halogen-containing reactive group to be reacted in solvent with the alkali metal compound is first dried as a preparatory step before reacting the polymer with the alkali metal compound in the solvent. Such a drying step may be conducted in any suitable manner for the purpose of minimizing or removing adsorbed water from the polymer, as water may interfere with the reaction. One acceptable non-limiting method for drying the polymers is to oven-dry them in a vacuum oven at a temperature suitable for the polymer chosen. For a polyarylene polymer, temperatures of about 100° C. to about 200° C., more preferably about 110° C. to about 120° C. are suitable. Oven drying should occur until the polymer is at least substantially dry, and for approximately at least 10 hours, preferably at least 15 hours, and most preferably about hours, with the understanding that drying times may also vary depending on the polymer and the level of adsorbed water in the pre-treated polymer. Drying can be verified via various types of moisture analysis, for example, Karl Fischer coulometric titration of the polymer dissolved in THF, measuring the dew point on an air dryer, or by loss of weight via thermogravimetric analysis (TGA) at temperatures less than about 250'C.

Once the dried organic polymer having the halogen-containing reactive group(s) is dissolved in the solvent and reacted with the alkali metal compound, an intermediate forms having a carbocation. This intermediate and the continuing reaction is then quenched by reacting the intermediate having the carbocation with acetic acid or a similar acetate group containing acid to form a dehalogenated organic polymer.

One reaction scheme for this reaction using a polyarylene polymer wherein the halogen-containing reactive group is diphenyl bromine, is shown below in reaction scheme C, wherein R represents the polymer chain of formula (III) above including the first phenyl group in the terminal, diphenyl bromine group.

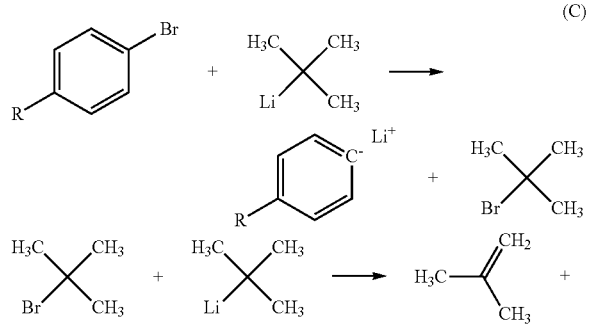

(C)

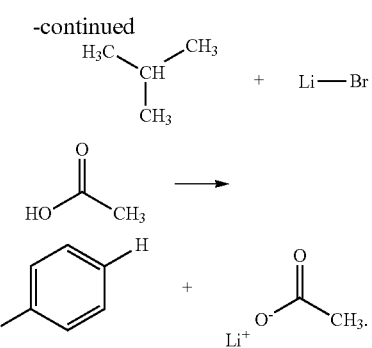

-continued

While the above mechanism shows a preferred method for dehalogenation herein, other reactions and methods for removing halogen from such organic polymers may also be used within the scope of the invention. See, for example, J. Moon et al., "Hydrogenolysis of Aryl Halides by Hydrogen Gas and Hydrogen Transfer over Palladium-Supported Catalysts," vol. 3, issue 6, Comptes Rendus L'Académie des Sciences—Chemistry, pp. 465-470 (November 2000). Dehalogenation may also be carried out via treatments with Grignard reagents. Grignard Degradation, Comprehensive Organic Name Reactions and Reagents, pp. 1271-1272 (September 2010).

After dehalogenation of the organic polymer, the dehalogenated organic polymer can be introduced into a cross-linking reaction and will provide enhanced performance to such reaction. Any suitable graft, reaction, or similar cross-linking reaction may be used. Preferably cross-linking occurs using a cross-linking compound as described above.

Thus, an organic polymer composition may be formed including the dehalogenated organic polymer and a cross-linking compound. Any suitable cross-linking compound that would create a cross-linked organic polymer from the dehalogenated organic polymer may be used. As an example of one such system, a dehalogenated organic polymer having an aromatic group in the backbone, may be cross-linked using a cross-linking compound that is preferred is one having a structure noted above according to formula (IV):

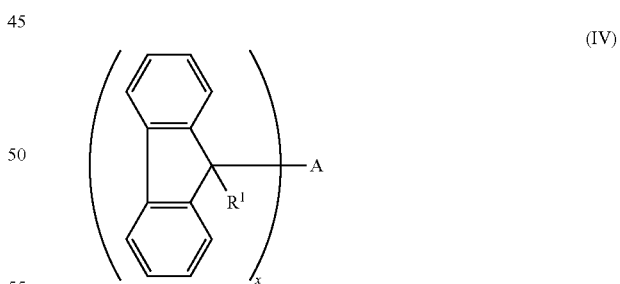

(IV)

wherein A is an arene moiety having a molecular weight of less than 10,000 g/mol, $R^1$ is selected from a group consisting of hydroxide (—OH), amine (—$NH_2$), halide, ether, ester, or amide, and x is about 2.0 to about 6.0.

One or more cross-linking compounds is/are present in the cross-linking composition and may be combined with the dehalogenated organic polymers in such compositions.

The arene moiety A on the cross-linking compound above provides the cross-link site for forming more complex cross-linking compound structures, including, for example, without limitation:

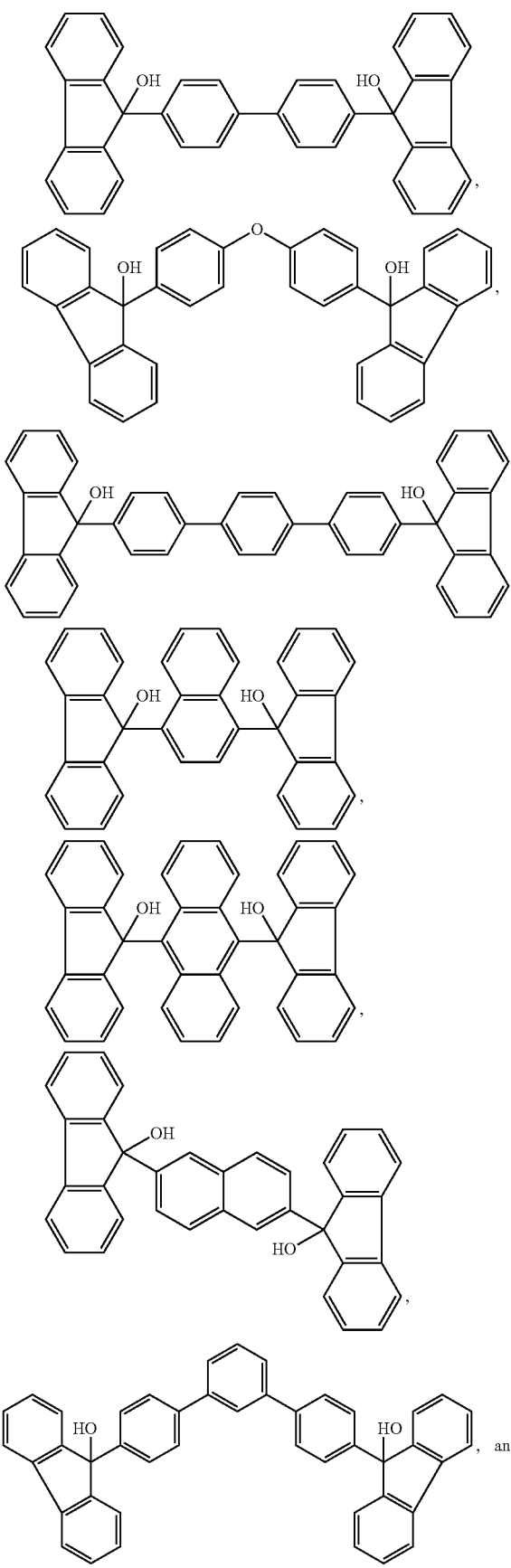
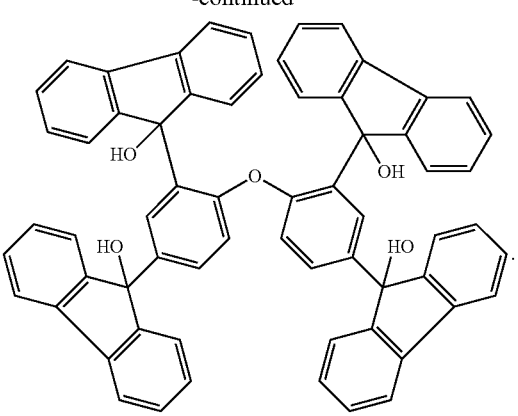
The arene moiety A may be varied to have different structures, including, but not limited to the following:
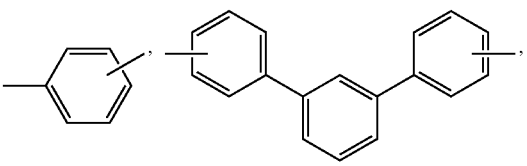
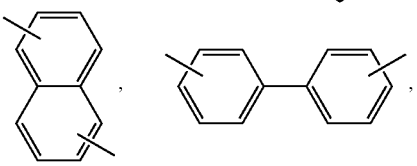
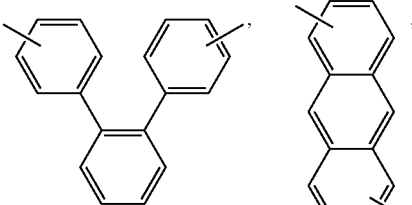
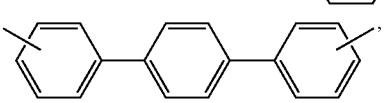
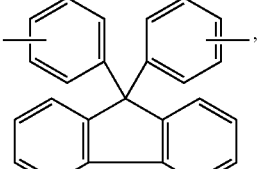
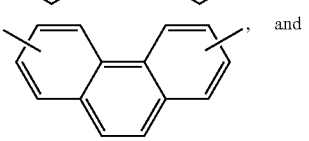
, and
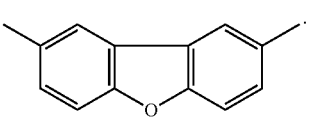
In addition, the arene moiety A is most preferably the diradical of 4,4'-biphenyl, or

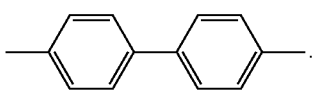

The arene moiety A may also be functionalized, if desired, using one or more functional groups such as, for example, and without limitation, sulfate, phosphate, hydroxyl, carbonyl, ester, halide, or mercapto. The cross-linking compound can be formed as noted above.

The cross-linking composition and the organic polymer composition also contain one or more cross-linking reaction additive(s) as rate-controlling compounds, that is, inhibitors.

The cross-linking reaction additive(s) are preferably the organic acids and/or an acetate compounds noted above and should be capable of reacting with the cross-linking compound(s) to form a reactive intermediate(s) in oligomeric form. Such reactive intermediate oligomer(s) should be capable of cross-linking the dehalogenated organic polymer to have a desired effect.

The cross-linking reaction additive(s) include organic acids and/or acetate compounds, which can promote oligomerization of the cross-linking compound. In one embodiment, the oligomerization can be carried out by acid catalysis using one or more organic acid(s), including glacial acetic acid, acetic acid, formic acid, lactic acid, citric acid, oxalic acid, uric acid, benzoic acid and similar compounds. An oligomerization reaction using one of the cross-linking compounds is shown above.

In other embodiments, inorganic acetate compounds, such as those having a structure according to formula (II) may also be used instead of or in combination with the organic acids:

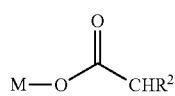

(II)

wherein M is a Group I or a Group II metal. $R^2$ in Formula (II) may preferably be an alkyl, aryl or aralkyl group. For example, $R^2$ may be a hydrocarbon group of 1 to about 30 carbon atoms, preferably about 1 to about 15 carbon atoms, including normal chain and isomeric forms of methyl, ethyl, propyl, butyl, pentyl, heptyl, octyl, nonyl, decyl, ethenyl, propenyl, butenyl, hexenyl, heptenyl, octenyl, nonenyl, decenyl, and the like. $R^2$ may also have from 0 to about 10 ester or ether groups, and more preferably about 0 to about 5 such groups, along or in a chain of the hydrocarbon group. Suitable $R^2$ aryl and aralkyl groups, including those based on phenyl, naphthyl, and similar groups, which may each include optional lower alkyl groups on the aryl structure of from 0 to about 5 carbon atoms. $R^2$ may further include 0 to about 5 functional groups if desired such as sulfate, phosphate, hydroxyl, carbonyl, ester, halide, mercapto and/or potassium on the structure.

Oligomerization of the cross-linking compound with an acetate compound can afford the same resultant oligomerized cross-linking composition as achieved when adding an organic acid. The cross-linking reaction additive may be lithium acetate hydrate, sodium acetate, potassium acetate, rubidium acetate, cesium acetate, francium acetate, beryllium acetate, magnesium acetate, calcium acetate, strontium acetate, barium acetate, and/or radium acetate, and salts and derivatives thereof. More preferably, the cross-linking reaction additive is lithium acetate hydrate, sodium acetate and/or potassium acetate, and salts and derivatives of such compounds. An oligomerization reaction using of one of the cross-linking compounds is shown above.

The cross-linking composition preferably has a weight percentage ratio of the cross-linking compound to the cross-linking reaction additive of about 10:1 to about 10,000:1, and more preferably about 20:1 to about 1000:1 for achieving the best results. In making the cross-linking composition, in one embodiment, the components are combined prior to addition of a dehalogenated organic polymer to make an organic polymer composition according to the invention. Alternatively, they may all be combined simultaneously.

The amount of the cross-linking compound in the cross-linking composition is preferably about 70% by weight to about 98% by weight, more preferably about 80% by weight to about 98% by weight, and most preferably about 85% by weight to about 98% by weight based on the weight of the cross-linking composition. The amount of the cross-linking reaction additive in the cross-linking composition is preferably about 2% by weight to about 30% by weight, more preferably about 2% by weight to about 20% by weight, and most preferably about 2% by weight to about 15% by weight.

The organic polymer composition preferably has a weight percentage ratio of the dehalogenated organic polymer to the combined weight of the cross-linking compound and the cross-linking reaction additive of about 1:1 to about 100:1, and more preferably about 3:1 to about 10:1 for achieving the best results.

In making the organic polymer composition, it is preferred that the cross-linking compound and the cross-linking reaction additive components are combined prior to addition of a dehalogenated organic polymer to make an organic polymer composition. Alternatively, they may all be combined simultaneously.

The amount of the cross-linking compound in the organic polymer composition is preferably about 1% by weight to about 50% by weight, more preferably about 5% by weight to about 30% by weight, and most preferably about 8% by weight to about 24% by weight based on the total weight of an unfilled organic composition including the cross-linking compound, the cross-linking reaction additive and the dehalogenated organic polymer.

The amount of the cross-linking reaction additive in the organic polymer composition is preferably about 0.01% by weight to about 33% by weight, more preferably about 0.1% by weight to about 10% by weight, and most preferably about 0.2% by weight to about 2% by weight based on the total weight of an unfilled organic polymer composition including the cross-linking compound, the cross-linking reaction additive and the dehalogenated organic polymer.

The amount of dehalogenated organic polymer in the organic polymer composition is preferably about 50% by weight to about 99% by weight, more preferably about 70% by weight to about 95% by weight, and most preferably about 75% by weight to about 90% by weight based on the total weight of an unfilled organic polymer composition including the cross-linking compound, the cross-linking reaction additive and the dehalogenated organic polymer.

The organic polymer composition may further be filled and/or reinforced and include one or more additives to improve the modulus, impact strength, dimensional stability, heat resistance and electrical properties of composites and other finished articles of manufacture formed using the polymer composition. These additive(s) can be any suitable or useful additives known in the art or to be developed, as described above herein.

In making the organic polymer composition, it is preferred that the additive(s) is/are added to the composition along with or at about the same time that the oligomerized cross-linking composition (or the combined components thereof) is combined with the dehalogenated organic polymer to make an organic polymer composition, however, the manner of providing reinforcing fibers or other fillers may be according to various techniques for incorporating such materials and should not be considered to limit the scope of the invention. The amount of additives is preferably about 0.5% by weight to about 65% by weight based on the weight of the organic polymer composition, and more preferably about 5.0% by weight to about 40% by weight.

In addition, the organic polymer composition may further comprise other compounding ingredients, including stabilizers, flame retardants, pigments, plasticizers, surfactants, and/or dispersants such as those known or to be developed in the art to aid in the manufacturing process. In making the organic polymer composition, it is preferred that the one or more fillers is/are added to the organic polymer composition along with or at about the same time that the oligomerized crosslinking composition (or the combined components thereof) is combined with the organic polymer to make an organic polymer composition, however, as noted above, the manner of providing such materials may be according to various techniques and should not be considered to limit the scope of the invention. The amount of the compounding ingredients that can be combined into the organic polymer composition, if used, is preferably about 5% by weight to about 60% by weight of a total of such ingredients based on the weight of the organic polymer composition, more preferably about 10% by weight to about 40% by weight, and most preferably about 30% by weight to about 40% by weight.

In an embodiment of the method of cross-linking according to the invention, after providing, for example by manufacturing, a cross-linking composition as described herein, the cross-linking composition is heated to induce oligomerization of the cross-linking compound as in Examples 1 to 4 and as noted above.

In one embodiment of the method, the oligomerization occurs by acid catalysis. Acid catalysis is used when an organic acid is employed as the cross-linking additive. The $R^1$ functionality of the cross-linking compound of Formula (IV) is dissociated from the remainder of the compound to afford a carbocation which then can undergo a Friedel-Crafts alkylation of the organic polymer, resulting in bond formation. In another embodiment of the method of the present invention, oligomerization of the cross-linking compound may occur by doping. Doping is accomplished by physically mixing solid form reactants in the composition at lower temperatures of about −100° C. to about −300° C. prior to reacting the overall composition for curing and/or heat molding the resulting composition to form an article.

The cross-linking method may further comprise adding the reacted oligomerized cross-linking composition to a debrominated organic polymer to form a cross-linkable composition. The unmodified cross-linking compound may be added directly to the dehalogenated organic polymer and blended with the cross-linking reaction additive to simultaneously oligomerize and bind to the dehalogenated organic polymer. Once the reactive oligomerized cross-linking compound reacts with the dehalogenated organic polymer, the rate of cross-linking of the dehalogenated organic polymer occurs at a later time in the curing process as compared to the rate of cross-linking that would occur in that organic polymer composition without dehalogenation treatment and using the same cross-linking system having the inhibitor additives as noted above or other prior art cross-linking systems. The result is the ability to more easily use traditional molding techniques and a controlled longer cross-linking time to form completely filled molds and excellent manufactured heat molded products.

Powders of the organic polymer compositions of the present invention can be made into pellets, and the pellets subjected to a heat molding process. Heat molding of the organic polymer compositions can be accomplished by many different means already known or to be developed in the art, including extrusion, injection molding, compression molding and/or injection/compression molding. Pellets of an organic polymer composition of the present invention may be injection molded, for example, on an Arbug® 38-ton injection molding machine with a cold runner system that includes a hot sprue.

Heat molding to form an article of manufacture may be accomplished by any method known or to be developed in the art including but not limited to heat cure, cure by application of high energy, heat cure, press cure, steam cure, a pressure cure, an e-beam cure or cure by any combination of means, etc. Post-cure treatments may also be applied, if desired. The organic polymer compositions of the present invention may be cured by exposing the composition to temperatures greater than about 250° C. to about 500° C., and more preferably about 350° C. to about 450° C.

The compositions and/or the methods described above may be used in or to prepare articles of manufacture of downhole tools and applications used in the petrochemical industry. Particularly, articles manufacture may be one or more of acid-resistant coatings, chemical-casted films, extruded films, solvent-casted films, blown films, encapsulated products, insulation, packaging, composite cells, connectors, and seating assemblies in the shape of O-rings, V-rings, U-cups, gaskets, bearings, valve seats, adapters, wiper rings, chevron back-up rings, and tubing.

The invention will now be further described in accordance with the following, non-limiting example:

EXAMPLE 6

In the following example, DSC data was collected on a TA Instruments Model Q100DSC at a heating rate of 20° C./min.

A 3 L, 3-neck round-bottomed flask was charged with 1800 mL of THF from a freshly opened bottle and 150 g of a dried polyarylene polymer having a backbone as shown in formula III shown above and at least biphenyl bromine end group on average. The flask was fitted with a mechanical stirrer (half-moon blade), septum port and a Claison head with thermometer an a nitrogen inlet. The flask was kept under nitrogen. For the few minutes during setup and before nitrogen blanketing, the materials were handled in ambient air. The reactor was stirred at room temperature until the organic polyarylene polymer was dissolved which took about 1 hour. The reactor was cooled to less than −70° C. using a dry ice/acetone bath.

With the reactor stirring at 500 to 800 rpm, t-butyllithium was added via cannula at a rate which maintained the reactor temperature below −65° C. This took about 15 min. As the polymer was lithiated, the solution became more viscous. After 2 hours at less than 70° C., glacial acetic acid was added to neutralize the lithiated polymer. The cooling bath was removed and the reactor was allowed to warm with no bath. When the temperature was above 0° C., the reaction was stirred at 100 to 200 rpm while continuing to warm to room temperature. After stirring for about 16 hours, the reaction mixture was filtered to remove an gel. The polymer was precipitated by pouring the filtrate into rapidly stirred methanol. The debrominated polymer was separated via vacuum filtration and dried under vacuum at 240° C. to remove any adsorbed methanol.

A GPC analysis showed that the polymer molecular weight remained stable after debromination treatment with no major increases due to crosslinking or decreases due to chain scission. See Table 4 below (wherein Mw is weight average molecular weight) and the molecular weight distribution plot below showing a comparison of the starting organic polymer and the debrominated polymer.

TABLE 4

| Sample Mn | | Mw | PDI |
|---|---|---|---|
| Starting Organic Polymer | 22,600 9 | 3,200 | 4.1 |
| Debrominated Organic Polymer | 23,300 9 | 6,300 | 4.1 |

The debrominated and starting polymers of the Example were crosslinked using a cross-linking compound having a structure as shown below as (D) lithium acetate as a cross-linking reaction additive.

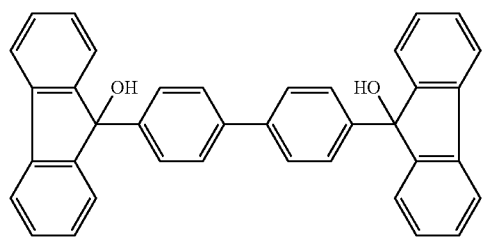

(D)

Figure 5:
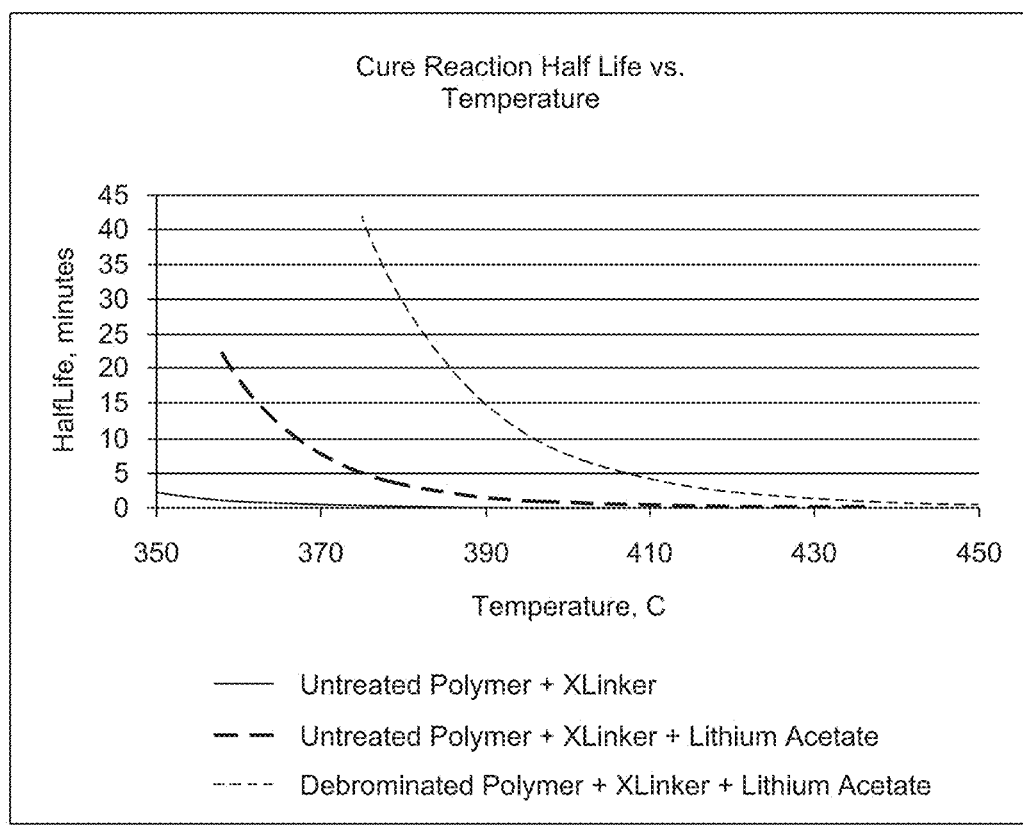
FIG. 5 is a graphical representation described in Example 6 as Graph A.
Figure 6:
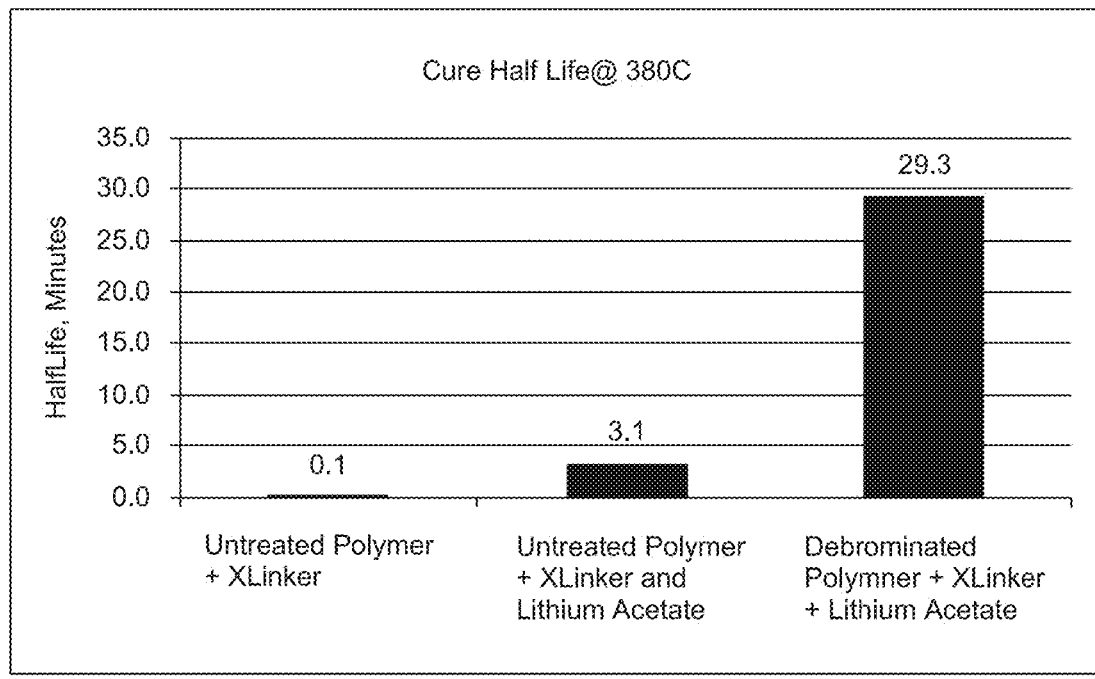
FIG. 6 is a graphical representation described in Example 6 as Graph B.

Using the Borchard-Daniels method noted above, the plots below in Graph A of FIG. 5 and Graph B of FIG. 6 show the improvement in half life achieved with the debromination treatment Lithium acetate yielded a half-life change of less than 1 minute to 3 minutes at a temperature of 380° C. The use of the same formulation with a debrominated polymer yielded a half life of approximately 30 minutes. In Graph A, the upper curve represents the debrominated polymer cross-linked with 20% of the cross-linking compound noted above and lithium acetate as a cross-linking reactive additive as an inhibitor. The middle curve represents the starting polymer (without debromination treatment) cross-linked with the same amount of cross-linking compounds noted above and using the lithium acetate inhibitor. The lower curve represents the untreated original polymer (without debromination treatment) cross-linked using the same amount of the cross-linking compound noted above but without the additional lithium acetate inhibitor. Graph B includes these same three materials exemplified in Graph A, but compares the half life of each at 380° C.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A composition comprising a cross-linking compound and a cross-linking reaction additive selected from an organic acid and/or an acetate compound, wherein the cross-linking compound has a structure according to formula (IV):

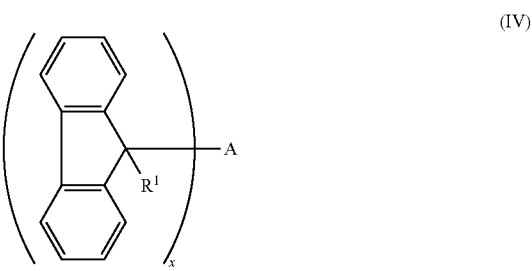

(IV)

wherein A is an arene moiety having a molecular weight of less than 10,000 g/mol, $R^1$ is selected from the group consisting of hydroxide (—OH), amine (—$NH_2$), halide, ether, ester, or amide, and x is about 2.0 to about 6.0, wherein the cross-linking reaction additive is capable of reacting with the cross-linking compound to form a reactive intermediate in the form of an oligomer, which reactive intermediate oligomer is capable of cross-linking an organic polymer.

2. The composition according to claim 1, wherein the cross-linking compound has a structure selected from the group consisting of

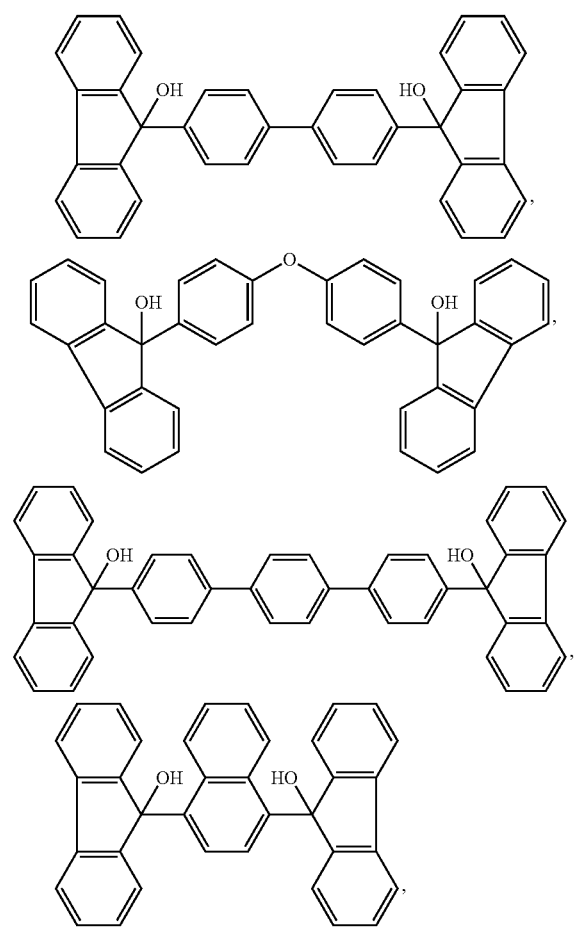

-continued

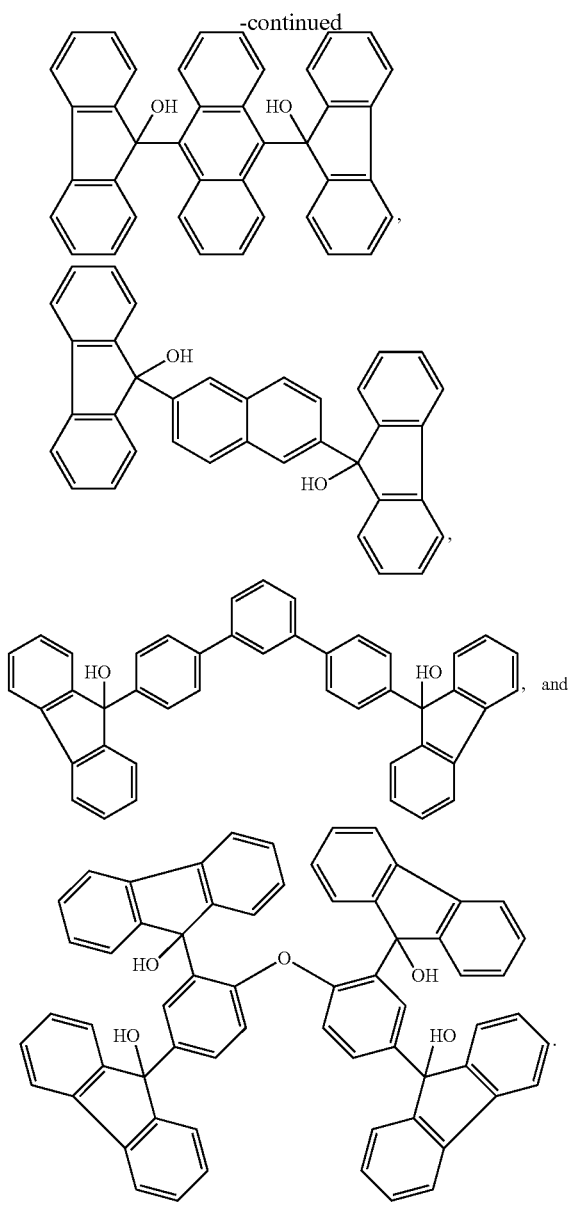

3. The composition according to claim 1, wherein the arene moiety has a molecular weight of about 1,000 g/mol to about 9,000 g/mol.

4. The composition according to claim 3, wherein the arene moiety has a molecular weight of about 2,000 g/mol to about 7,000 g/mol.

5. The composition according to claim 1, wherein the cross-linking reaction additive is an organic acid selected from glacial acetic acid, formic acid, and/or benzoic acid.

6. The composition according to claim 1, wherein the cross-linking reaction additive is an acetate compound having a structure according to formula (II):

wherein M is a Group I or a Group II metal; and $R^2$ is a alkyl, aryl or aralkyl group, wherein the alkyl group comprises a hydrocarbon group of 1 to about 30 carbon atoms which has from 0 to about 10 ester or ether groups along or in a chain or structure of the group, and wherein $R^2$ comprises 0 to about 10 functional groups selected from sulfate, phosphate, hydroxyl, carbonyl, ester, halide, mercapto or potassium.

7. The composition according to claim 6, wherein the acetate compound is selected from lithium acetate hydrate sodium acetate, and/or potassium acetate, and salts and derivatives thereof.

8. The composition according to claim 1, wherein the weight percentage ratio of the cross-linking compound to the cross-linking reaction additive is about 10:1 to about 10,000:1.

9. The composition according to claim 8, wherein the weight percentage ratio of the cross-linking compound to the cross-linking reaction additive is about 20:1 to about 1000:1.

10. The composition according to claim 1, further comprising at least one organic polymer, wherein the cross-linking reaction additive is capable of reacting with the cross-linking compound to form a reactive intermediate in the form of an oligomer, which reactive intermediate oligomer is capable of cross-linking the organic polymer.

11. The organic polymer composition according to claim 10, wherein the organic polymer is selected from poly (arylene ether)s, polysulfones, polyethersulfones, polyimides, polyamides, polyureas, polyurethanes, polyphthalamides, polyamide-imides, poly(benzimidazole)s and polyaramids.

12. The organic polymer composition according to claim 11, wherein the organic polymer is a poly(arylene ether) including polymer repeating units having the following structure:

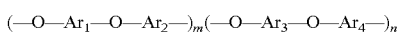

wherein $Ar^1$, $Ar^2$, $Ar^3$ and $Ar^4$ are identical or different aryl radicals, m=0 to 1.0, and n=1−m.

13. The organic polymer composition according to claim 12, wherein the organic polymer is a poly(arylene ether), m is 1 and n is 0 and the polymer has repeating units having the structure of formula (V):

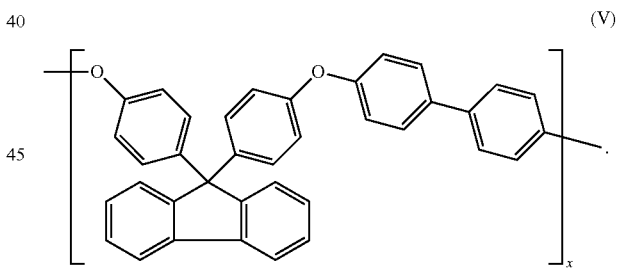

14. The organic polymer composition according to claim 10, wherein the cross-linking reaction additive is an organic acid selected from glacial acetic acid, formic acid and/or benzoic acid.

15. The organic polymer composition according to claim 10, wherein the cross-linking reaction additive is an acetate compound having a structure according to formula (II):

wherein M is a Group I or a Group II metal; and $R^2$ is a alkyl, aryl or aralkyl group, wherein the alkyl group comprises a hydrocarbon group of 1 to about 30 carbon atoms which has from 0 to about 10 ester or ether groups along or in a chain or structure of the group, and wherein $R^2$ comprises 0 to about 10 functional groups selected from sulfate, phosphate, hydroxyl, carbonyl, ester, halide, mercapto or potassium.

16. The organic polymer composition according to claim 10, wherein the weight percentage ratio of the organic polymer to the combined weight of the cross-linking compound and the cross-linking reaction additive is about 1:1 to about 100:1.

17. The organic polymer composition according to claim 16, wherein the weight percentage ratio of the organic polymer to the combined weight of the cross-linking compound and the cross-linking reaction additive is about 3:1 to about 10:1.

18. The organic polymer composition according to claim 10, wherein the composition further comprises at least one additive selected from continuous or discontinuous, long or short, reinforcing fibers selected from carbon fibers, glass fibers, woven glass fibers, woven carbon fibers, aramid fibers, boron fibers, polytetrafluorethylene fibers, ceramic fibers, polyamide fibers; and one or more fillers selected from carbon black, silicate, fiberglass, calcium sulfate, boron, ceramic, polyamide, asbestos, fluorographite, aluminum hydroxide, barium sulfate, calcium carbonate, magnesium carbonate, silica, alumina, aluminum nitride, borax (sodium borate), activated carbon, pearlite, zinc terephthalate, graphite, talc, mica, silicon carbide whiskers or platelets, nanofillers, molybdenum disulfide, fluoropolymer, carbon nanotubes and fullerene tubes.

19. The organic polymer composition according to claim 18, wherein the composition comprises about 0.5% to about 65% by weight of the at least one additive.

20. The organic polymer composition according to claim 10, wherein the composition further comprises a stabilizer, a flame retardant, a pigment, a plasticizer, a surfactant, and or a dispersant.

21. A molded article formed from the composition according to claim 10.

22. The molded article according to claim 21, wherein the article is molded using extrusion, injection molding, blow molding, blown film molding, compression molding or injection/compression molding.

23. An article of manufacture formed from the composition according to claim 10, wherein the article of manufacture is selected from acid-resistant coatings; chemical-casted films; extruded films; solvent-casted films; blown films; encapsulated products; insulation; packaging; composite cells; connectors; sealing assemblies, including O-rings, V-rings, U-cups, gaskets; bearings; valve seats; adapters; wiper rings; chevron back-up rings; and tubing.

24. An organic polymer composition for use in forming a cross-linked organic polymer, comprising:
 an organic polymer; and
 a reactive cross-linking oligomer which is a reaction product of a cross-linking compound having the structure of formula (IV):

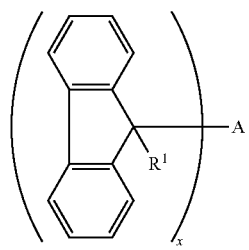

(IV)

wherein A is an arene moiety having a molecular weight of less than 10,000 g/mol, $R^1$ is selected from a group consisting of hydroxide (—OH), amine (—$NH_2$), halide, ether, ester, or and amide, and x is about 2.0 to about 6.0, and a cross-linking reaction additive selected from an organic acid and/or an acetate compound.

25. A molded article formed from the composition of claim 24.

26. A method of controlling the cross-linking reaction rate of a cross-linking compound for use in cross-linking an organic polymer, comprising:
 a) providing a cross-linking composition comprising a cross-linking compound and a cross-linking reaction additive selected from an organic acid and/or an acetate compound, wherein the cross-linking compound has the structure according to formula (IV):

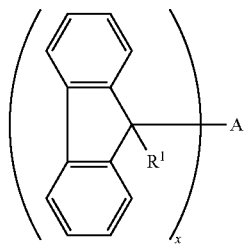

(IV)

wherein A is an arene moiety having a molecular weight of less than 10,000 g/mol, $R^1$ is selected from a group consisting of hydroxide (—OH), amine (—$NH_2$), halide, ether, ester, or amide, and x is about 2.0 to about 6.0, wherein the cross-linking reaction additive is capable of reacting with the cross-linking compound to form a reactive intermediate in the form of an oligomer for cross-linking an organic polymer; and
 b) heating the cross-linking composition such that oligomerization of the cross-linking compound occurs.

27. The method according to claim 26, wherein step (b) further comprises heating the cross linking composition before heat molding.

28. The method according to claim 26, wherein the cross-linking reaction additive is an organic acid selected from glacial acetic acid, formic acid and/or benzoic acid, and/or an acetate compound selected from lithium acetate, hydrate sodium acetate, and/or potassium acetate, and salts and derivatives thereof.

29. The method according to claim 26, further comprising combining the cross-linking compound and the cross-linking reaction additive in solid form in step (a).

30. The method according to claim 26, further comprising combining the cross-linking compound and the cross-linking reaction additive in a solvent in step (a) and reacting the cross-linking compound and the cross-linking reaction additive to form a reactive oligomerized cross-linking compound.

31. The method according to claim 30, further comprising
 (c) adding the reactive oligomerized cross-linking compound to an organic polymer to form a cross-linkable composition and
 (d) cross-linking the organic polymer composition to form a cross-linked organic polymer.

32. The method according to claim 31, further comprising adding at least one additive in step (c).

33. The method according to claim 26, wherein the organic polymer is selected from poly(arylene ether)s, polysulfones, polyethersulfones, polyimides, polyamides, polyureas, polyurethanes, polyphthalamides, polyamide-imides, poly(benzimidazole)s and/or polyaramids.

34. The method according to claim 33, wherein the organic polymer is a poly(arylene ether) including polymer repeating units having the following structure:

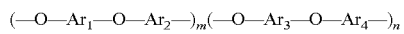

wherein Ar¹, Ar², Ar³ and Ar⁴ are identical or different aryl radicals, m=0 to 1.0, n=1−m.

35. An organic polymer composition for use in forming a cross-linked organic polymer, comprising:
a dehalogenated organic polymer and
at least one cross-linking compound; wherein the dehalogenated organic polymer is formed by a process comprising reacting an organic polymer having at least one halogen-containing reactive group with an alkali metal compound to break a bond between the organic polymer having the at least one halogen-containing reactive group and a halogen atom in the at least one halogen-containing reactive group to form an intermediate.

36. The organic polymer composition according to claim 35, wherein the dehalogenated organic polymer is a debrominated organic polymer.

37. The organic polymer composition according to claim 35, wherein the cross-linking compound has a structure according to formula (IV):

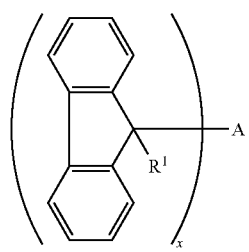

(IV)

wherein A is an arene moiety having a molecular weight of less than 10,000 g/mol R¹ is selected from a group consisting of hydroxide (—OH), amine (—NH₂), halide, ether, ester, or amide, and x is about 2.0 to about 6.0.

38. The organic polymer composition according to claim 35, further comprising a cross-linking reaction additive selected from an organic acid and/or an acetate compound, wherein the cross-linking reaction additive is capable of reacting with the cross-linking compound to form a reactive intermediate in the form of an oligomer, which reactive intermediate oligomer is capable of cross-linking the dehalogenated organic polymer.

39. The organic polymer composition according to claim 35, wherein the dehalogenated organic polymer is a polymer selected from poly(arylene ether)s, polysulfones, polyethersulfones, polyimides, polyamides, polyureas, polyurethanes, polyphthalamides, polyamide-imides, poly(benzimidazole)s and polyaramids.

40. The organic polymer composition according to claim 39, wherein the dehalogenated organic polymer is a poly(arylene ether) including polymer repeating units in its backbone having the following structure:

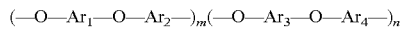

wherein Ar¹, Ar², Ar³ and Ar⁴ are identical or different aryl radicals, m=0 to 1.0, and n=1−m.

41. The organic polymer composition according to claim 40, wherein the dehalogenated organic polymer is a poly(arylene ether), m is 1 and n is 0 and the polymer has repeating units along its backbone having the structure of formula (V):

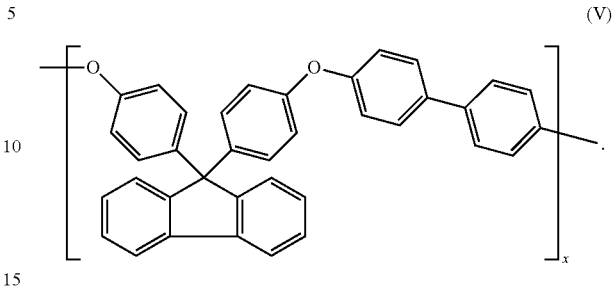

(V)

42. The organic polymer composition according to claim 35, wherein the composition further comprises at least one additive selected from continuous or discontinuous, long or short, reinforcing fibers selected from carbon fibers, glass fibers, woven glass fibers, woven carbon fibers, aramid fibers, boron fibers, polytetrafluoroethylene fibers, ceramic fibers, polyamide fibers; and one or more fillers selected from carbon black, silicate, fiberglass, calcium sulfate, boron, ceramic, polyamide, asbestos, fluorographite, aluminum hydroxide, barium sulfate, calcium carbonate, magnesium carbonate, silica, alumina, aluminum nitride, borax (sodium borate), activated carbon, pearlite, zinc terephthalate, graphite, talc, mica, silicon carbide whiskers or platelets, nanofillers, molybdenum disulfide, fluoropolymer, carbon nanotubes and fullerene tubes.

43. The organic polymer composition according to claim 35, wherein the dehalogenated organic polymer is formed by
reacting an organic polymer having at least one halogen-containing reactive group with an alkali metal compound to break a bond between the organic polymer having the at least one halogen-containing reactive group and a halogen atom in the at least one halogen-containing reactive group, and to form an intermediate; and
reacting the intermediate with acetic acid to form the dehalogenated organic polymer.

44. The organic polymer composition according to claim 43, wherein the alkali metal compound is selected from the group consisting of R³—M', wherein M' is an alkali metal and R³ is H or a branched or straight chain organic group selected from alkyl, alkenyl, aryl and aralkyl groups of from 1 to about 30 carbon atoms having from 0 to about 10 ester or ether groups along or in a chain or structure of the group, and wherein R³ may be substituted or unsubstituted.

45. The organic polymer composition according to claim 44, wherein the alkali metal compound is t-butyllithium.

46. The organic polymer composition according to claim 43, wherein the halogen-containing reactive group is a bromine-containing reactive group.

47. The organic polymer composition according to claim 43, wherein the organic polymer having at least one halogen-containing end group is reacted with the alkali metal compound in a solvent and the organic polymer having the at least one halogen-containing end group is dried prior to reacting in the solvent.

48. A molded article formed from the composition according to claim 35.

49. A method of controlling the cross-linking reaction rate of an organic polymer having at least one halogen-containing reactive group during a cross-linking reaction, comprising:

a) reacting the organic polymer having at least one halogen-containing reactive group with an alkali metal compound to break a bond between the organic polymer having the at least one halogen-containing reactive group and a halogen atom in the at least one halogen-containing reactive group, and to form an intermediate having carbocation;

b) reacting the intermediate having the carbocation with acetic acid to form a dehalogenated organic polymer; and c) crosslinking the dehalogenated organic polymer using a crosslinking reaction.

50. The method according to claim 49, wherein the at least one halogen-containing reactive group is a terminal group and the organic polymer having the at least one halogen-containing reactive group is a polymer selected from poly(arylene ether)s, polysulfones, polyethersulfones, polyimides, polyamides, polyureas, polyurethanes, polyphthalamides, polyamide-imides, poly(benzimidazole)s, and polyaramids.

51. The method according to claim 49, wherein the at least one halogen-containing reactive group is represented by —$R^4$—$(X)_p$, wherein $R^4$ is carbon or a branched or straight chain organic group selected from alkyl, alkenyl, aryl and aralkyl groups of from 1 to about 30 carbon atoms having from 0 to about 10 ester or ether groups along or in a chain or structure of the group, and wherein $R^4$ may be substituted or unsubstituted; and X is a halogen atom and p is an integer that is 1 or 2.

52. The method according to claim 49, wherein the alkali metal compound is selected from the group consisting of $R^3$—M', wherein M' is an alkali metal and $R^3$ is H or a branched or straight chain organic group selected from alkyl, alkenyl, aryl and aralkyl groups of from 1 to about 30 carbon atoms having from 0 to about 10 ester or ether groups along or in a chain or structure of the group, and wherein $R^3$ may be substituted or unsubstituted.

53. The method according to claim 52, wherein the alkali metal compound is t-butyllithium.

54. The method according to claim 49, wherein the organic polymer having the at least one halogen-containing end group is reacted with the alkali metal compound in a solvent.

55. The method according to claim 54, wherein the solvent is capable of dissolving the organic polymer having the at least one halogen-containing reactive group and is free of functional groups that react with the halogen in the halogen-containing reactive group under reaction conditions for step (a).

56. The method according to claim 55, wherein the solvent is selected from a heptane, a hexane, tetrahydrofuran, and a diphenyl ether.

57. The method according to claim 54, wherein the organic polymer having the at least one halogen-containing end group is dried prior to reacting with the alkali metal compound in the solvent.

58. The method according to claim 49, wherein step (a) occurs at a temperature of less than about −20° C.

59. The method according to claim 58, wherein step (a) occurs at a temperature of less than about −70° C. for a period of about 2 hours.

60. The method according to claim 49, wherein step (c) further comprises:

reacting the dehalogenated organic polymer with a cross-linking compound.

61. The method according to claim 60, wherein step (c) further comprises providing a cross-linking reaction additive selected from an organic acid and/or an acetate compound, wherein the cross-linking reaction additive is capable of reacting with the cross-linking compound to form a reactive intermediate in the form of an oligomer, which reactive intermediate oligomer is capable of cross-linking the dehalogenated organic polymer.

62. The method according to claim 61, further comprising before step (c) heating the cross-linking compound and the cross-linking reaction additive in a separate composition such that oligomerization of the cross-linking compound occurs to form the reactive intermediate oligomer.

63. The method according to claim 49, further comprising heat molding the cross-linked organic polymer to form a heat-molded article of manufacture.

64. The method according to claim 63, wherein the article of manufacture is heat molded using extrusion, injection molding, blow molding, blown film molding, compression molding or injection/compression molding.

65. The method according to claim 63, wherein the article of manufacture is selected from acid-resistant coatings; chemical-casted films; extruded films; solvent-casted films; blown films; encapsulated products; insulation; packaging; composite cells; connectors; sealing assemblies, including O-rings, V-rings, U-cups, gaskets; bearings; valve seats; adapters; wiper rings; chevron back-up rings; and tubing.

* * * * *

UNITED STATES PATENT AND TRADEMARK OFFICE
CERTIFICATE OF CORRECTION

PATENT NO. : 9,109,080 B2  
APPLICATION NO. : 14/059064  
DATED : August 18, 2015  
INVENTOR(S) : Kerry A. Drake et al.

Page 1 of 1

It is certified that error appears in the above-identified patent and that said Letters Patent is hereby corrected as shown below:

In the Claims

Column 44, line 32, the formula

"— $(O — Ar_1 — O — Ar_2 —)_m(— O — Ar_3 — O — Ar_4 —)_n$" of claim 12 should read as follows:

-- — $(O — Ar^1 — O — Ar^2 —)_m(— O — Ar^3 — O — Ar^4 —)_n$ --

Column 47, line 7, the formula

"— $(O — Ar_1 — O — Ar_2 —)_m(— O — Ar_3 — O — Ar_4 —)_n$" of claim 34 should read as follows:

-- — $(O — Ar^1 — O — Ar^2 —)_m(— O — Ar^3 — O — Ar^4 —)_n$ --

Column 47, line 63, the formula

"— $(O — Ar_1 — O — Ar_2 —)_m(— O — Ar_3 — O — Ar_4 —)_n$" of claim 40 should read as follows:

-- — $(O — Ar^1 — O — Ar^2 —)_m(— O — Ar^3 — O — Ar^4 —)_n$ --

Signed and Sealed this  
Nineteenth Day of April, 2016

Michelle K. Lee  
*Director of the United States Patent and Trademark Office*